United States Patent [19]

Orkin et al.

[11] Patent Number: 5,207,642
[45] Date of Patent: May 4, 1993

[54] CLOSED MULTI-FLUID DELIVERY SYSTEM AND METHOD

[75] Inventors: Fredric I. Orkin, Deerfield; Theodore Liber, Highland Park; Charles R. Smith, Libertyville; Kimball J. Knowlton, Lindenhurst, all of Ill.; Albin Huntley, Martinez, Calif.

[73] Assignee: Baxter International Inc., Deerfield, Ill.

[21] Appl. No.: 345,064

[22] Filed: Apr. 28, 1989

Related U.S. Application Data

[63] Continuation-in-part of Ser. No. 83,843, Aug. 7, 1987, Pat. No. 4,925,444.

[51] Int. Cl.$^5$ .................. A61M 31/00; A61M 37/00
[52] U.S. Cl. ........................... 604/65; 604/86; 604/123; 604/250; 604/905; 128/DIG. 13
[58] Field of Search .............. 604/65, 67, 245-246, 604/250, 80-82, 259, 260, 83, 86, 283, 284, 415, 905, 122-126; 222/639, 642, 643, 135, 145, 30, 27, 59; 141/99, 104, 105, 107; 128/DIG. 13, DIG. 12; 137/588

[56] References Cited

U.S. PATENT DOCUMENTS

| | | | |
|---|---|---|---|
| 2,954,028 | 9/1960 | Smith | 604/250 |
| 3,749,285 | 7/1973 | Latham, Jr. | |
| 4,038,982 | 8/1977 | Burke et al. | 604/65 |
| 4,094,318 | 6/1978 | Burke et al. | 604/245 |
| 4,464,172 | 8/1984 | Lichtenstein | 604/65 |
| 4,533,347 | 7/1985 | Deckert | 604/81 |
| 4,559,036 | 12/1985 | Wunsch | 604/81 |
| 4,559,045 | 12/1985 | Danby et al. | 604/250 |
| 4,673,390 | 6/1987 | Archibald | |
| 4,678,460 | 7/1987 | Rosner | |
| 4,705,506 | 10/1987 | Archibold | 604/81 |
| 4,706,368 | 11/1987 | Crissman, III | 248/125 |
| 4,769,017 | 9/1988 | Fath et al. | 604/283 |
| 4,828,545 | 5/1989 | Epstein et al. | 604/66 |

FOREIGN PATENT DOCUMENTS 0233115  8/1987  European Pat. Off. .
WO8602625  9/1986  PCT Int'l Appl. .

Primary Examiner—C. Fred Rosenbaum
Assistant Examiner—Mark Bockelman
Attorney, Agent, or Firm—Paul E. Schaafsma; Amy L. H. Rockwell; Paul C. Flattery

[57] ABSTRACT

An improved multiple fluid delivery system usable for the delivery of intravenous fluids to a patient from a plurality of fluid sources includes flexible tubing members for coupling the sources to a fluid junction member. The fluid junction member, wherein little or no interfluid mixing occurs, is coupled by an output conduit to a controllable pump. Output from the pump, via a further fluid flow conduit, can be coupled to the patient's catheter. The system can multiplex a plurality of different fluids. Spaced apart sequences of fluid quanta are injected into the output conduit from the fluid flow junction. The fluids are either mixed, or not, in the output conduit as desired. Operator interaction and control of the system can occur either through a display screen or by means of a bar code sensor. Hard copy records can be provided of fluid flow delivery schedules or other related information.

22 Claims, 29 Drawing Sheets

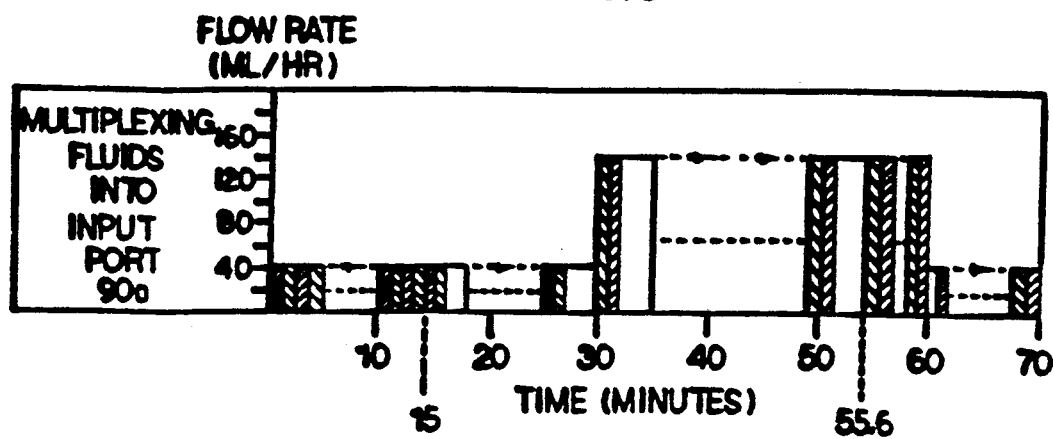
FIG. 11C
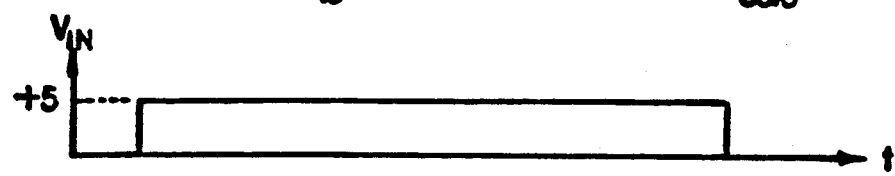
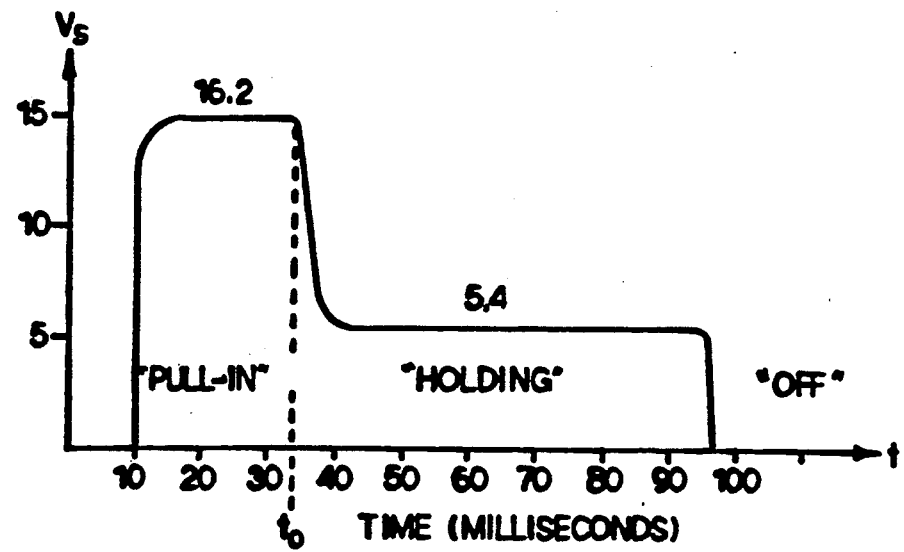
FIG. 9B

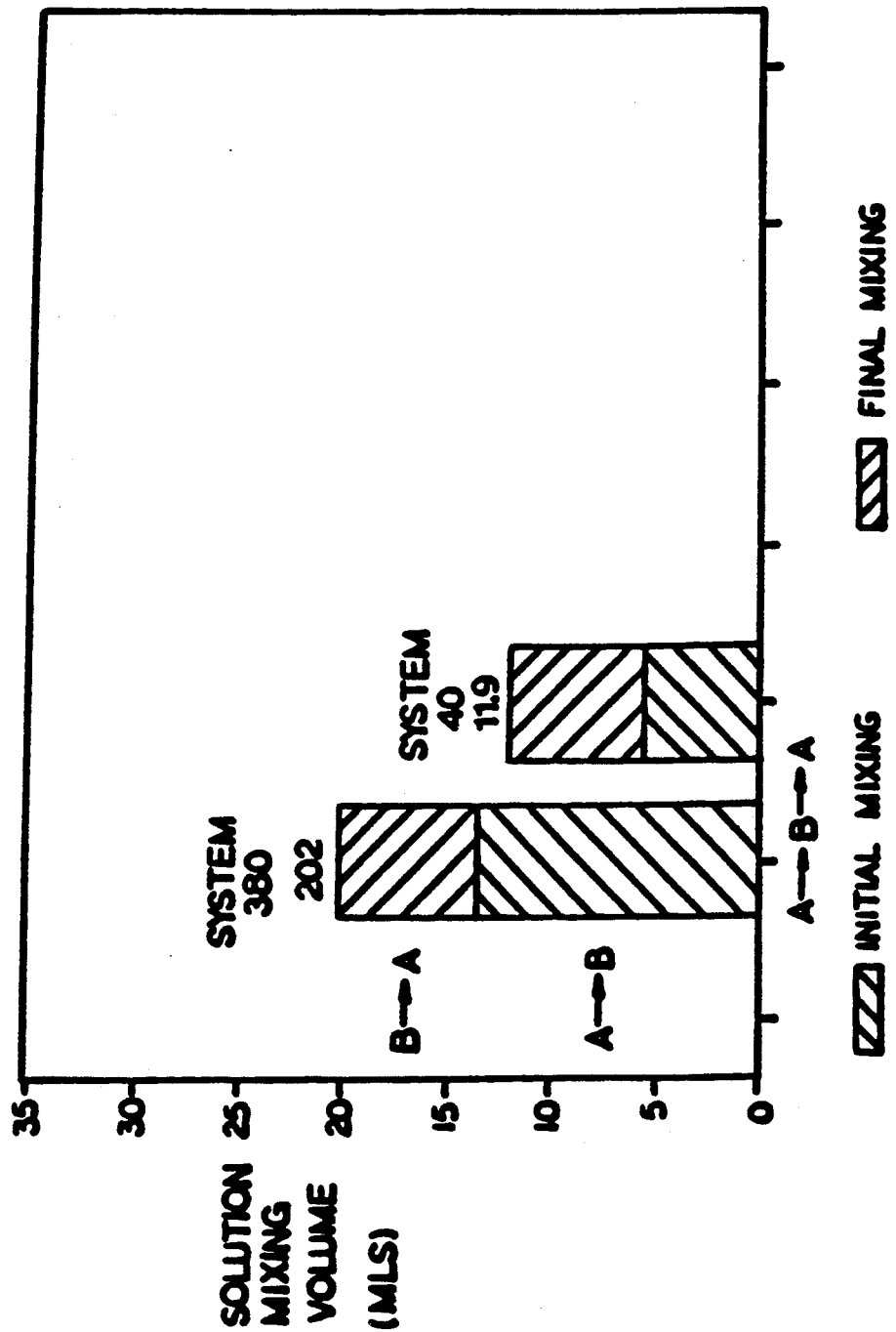

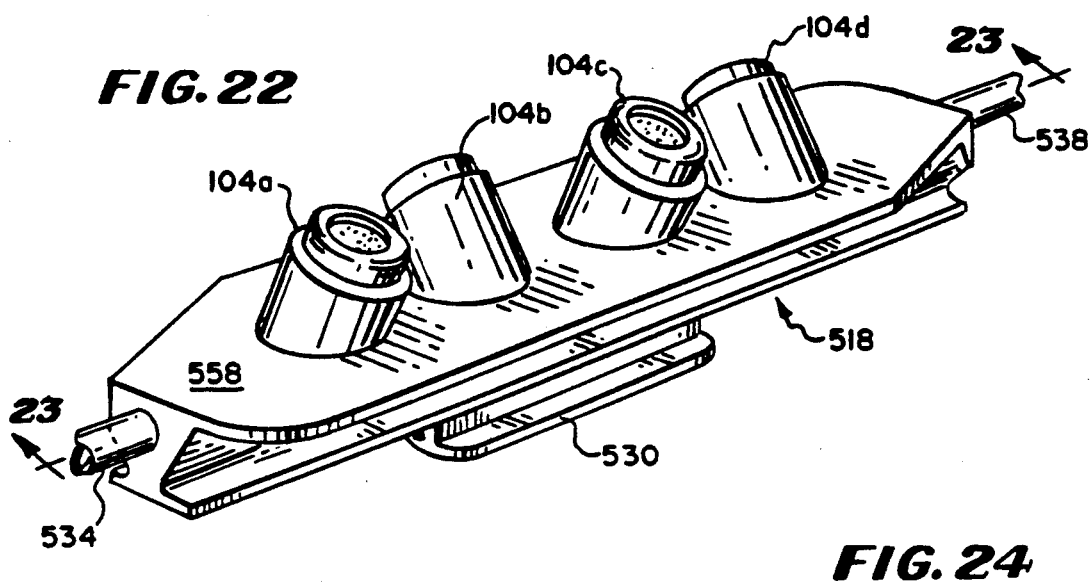
FIG. 22
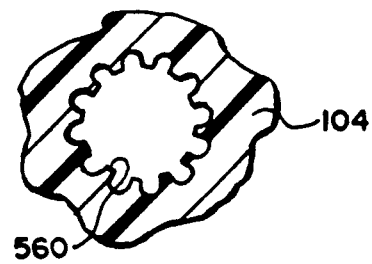
FIG. 24
FIG. 23

CLOSED MULTI-FLUID DELIVERY SYSTEM AND METHOD

This application is a continuation-in-part of patent application Ser. No. 07/083,843 filed Aug. 7, 1987 now U.S. Pat. No. 4,925,444.

FIELD OF THE INVENTION

The invention pertains to the field of drug delivery systems and methods. More particularly, the invention pertains to an improved apparatus and method for controllably providing a plurality of different fluids to a single fluid-flow junction for delivery in predetermined proportions at predetermined rates.

BACKGROUND OF THE INVENTION

The intravenous infusion of various types of medicated fluids into patients has become an important part of the treatment of many different diseases. In addition, such multiple fluid infusion programs have also become an important part of the treatment of patients with trauma or patients injured in accidents. Such patients often receive their acute treatment in intensive-care units. In many institutions, imuno-suppressed patients such as bone marrow and other transplant patients also receive multiple intravenous fluids over a substantial period of time.

Depending on the physician's orders, these fluids are delivered to the patient by means of a surgically inserted, main-line catheter or at a peripheral site, such as the patient's arm or leg. Because of the condition of many of these patients, it is especially critical that the correct drug doses be administered at the correct rates during the designated period of time. Further, many such patients become highly vulnerable to infections or may have depressed or damaged immune systems. Therefore, it is important to minimize, to the greatest extent possible, the potential entrance of infectious agents into the flow of fluids being administered.

Multiple fluid intraveneous infusion has been practiced in the prior art by hanging containers of solution from an IV administration pole. The pole might be mounted on wheels to make it transportable. An initial solution is hung, and using aseptic technique is coupled to the patient's catheter. The nurse or other health professional adjusts the rate of flow by timing the rate of fluid drops falling in a drip chamber while manually adjusting a clamp valve.

To add a second fluid without adding another injection site to the patient, a fluid-flow junction, sometimes referred to as a "Y" site, or a "Y" junction is provided. This junction is located in the initial fluid-flow delivery tube. The second container of solution is coupled into an unused input of the "Y" junction. The rate of flow of the two solutions can be readjusted by means of manually operable clamps and drip chambers associated with each of the solution containers and by adjusting the relative heights of the containers.

If a third solution is required, a second "Y" junction is provided and located in the administration line associated with the second fluid container. The third fluid-flow container is coupled into the second "Y" junction and the rates of flow are again, manually adjusted as before.

There have been a number of recognized problems associated with the above-described fluid-delivery systems. One immediate problem is the fact that use of gravity-flow and drop counting does not necessarily ensure that the desired flow rates to the patient will be maintained or will be sufficiently accurate. This is aggravated if the patient is to be moved such as for X-rays, cat scans or therapy. Such movement is difficult and cumbersome, while fluid is still being administered.

To overcome these problems it has become standard practice to use electrically powered infusion pumps which can be set to deliver a predetermined quantity of fluid through a fluid-flow conduit at a predetermined rate. Such pumps lend themselves to portable usage. Usually they are mounted right on the fluid delivery pole, which is itself mounted on casters. Such pumps are often provided with battery back-up to provide portability and to provide several hours of uninterrupted service in case of main power failure.

Known prior art systems do not provide for appropriate automatic control of the various substances being delivered. In addition, multiple lines may need to be run between the patient and the plurality of infusion pumps to provide the necessary multiple drug therapy.

A step in the direction of attempting to deal with this problem is illustrated in U.S. Pat. No. 4,512,764 issued to Wunsch. The Wunsch patent provides for a plurality of fluid-flow solution containers which can be interconnected by a fluid-flow transfer set and a set of manually operative valves. Output from the manually operable valve system is coupled to a single fluid-flow conduit. This conduit passes through a peristaltic pump and then on to the patient. The manually operable valves are opened and closed at various periods of time to deliver the desired fluids.

In another patent, U.S. Pat. No. 4,559,036 also to Wunsch, a computer controlled set of valves is illustrated. The system of this latter Wunsch patent includes either motor activated or solenoid controlled valves which are connected to the control unit. Further, this system provides for a timing cycle, during which various valves are independently and successively opened for predetermined time intervals to permit the flow of various fluids to a patient.

Other multiple-fluid infusion systems have also been proposed which include various types of electronic control units. One aspect of any such system is the fluid-flow delivery set Which is utilized in the apparatus. Some of the known delivery sets are relatively complex and expensive.

Extensive experience has taught that sterile, limited use, disposable, fluid-flow transfer sets can be cost-effective. Such sets can also be very effective in minimizing the possibility that infectious agents might inadvertently be delivered to the patient. However, such sterile, limited-use, transfer sets do not in themselves solve the problem of controlling the infusion of a variety of different fluids to produce a desired composite fluid flow.

One known alternate is to use a multiplicity of infusion pumps, each coupled to one or more sets of solution containers. In this embodiment, two or more lines, each associated with a respective infusion pump, are brought to the patient and are coupled in an aseptic fashion to the patient. Such systems tend to be very flexible and are assembled at the patient's bedside. Nevertheless, they result in a cluttered, confusing system and represent substantial control problems from the point of view of the delivered fluid flow.

From a practical perspective, there is always a problem in any arrangement having multiple IV infusion poles, multiple pumps, multiple electrical cords and multiple sets of lines running from the containers to the pumps and from the pumps to the patient. When an attempt is made to move the patient, all of the poles must be moved in unison. This is not too difficult with one pole. It can be manageable with two poles. It becomes very difficult with three poles.

There is thus a continuing need for a closed, relatively portable uncluttered system which will provide for multiple, essentially simultaneous delivery of a plurality of different sterile fluids under sterile conditions. Preferably such a system would provide the ability to reduce potential contamination problems by reducing the number and complexity of tubes and junction members necessary to effectuate delivery of the fluids.

Such a system preferably would provide the ability to prepare planned medications and fluid-flow delivery sequences which would extend over substantial periods of time such as 24 hours. Further, such systems would preferably utilize main-line catheters for the purpose of reducing the number of or eliminating various vein punctures usually necessary for the delivery process.

In addition, such a system should provide for the relatively long-term scheduling of delivered medications, such as over a 24 hour period. Further, such a system should provide assistance to the nursing staff of an institution in a variety of ways. The multiplicity of different infusion pumps should be reduced to the greatest extent possible.

The system should also be relatively user friendly and easy for the provider of care to work with. Further, such a system should assist in recordkeeping such as by generating hard-copy while at the same time being relatively silent in operation to avoid disturbing the patient and unobtrusive in function. One closed multiple-fluid delivery system is disclosed in parent application Ser. No. 083,843, filed Aug. 7, 1987, entitled CLOSED MULTI-FLUID DELIVERY SYSTEM AND METHOD, which is incorporated herein by reference.

SUMMARY OF THE INVENTION

In accordance with the present invention, an improved closed, multiple-fluid delivery system is provided, which system can deliver a plurality of preselected fluids in a preselected sequence via a closed fluid-flow delivery system to an output port.

The system includes a plurality of deformable fluid-flow tubing or conduit members. The tubing members can have a spike connector at one end for insertion into an access port of an intravenous fluid container. The system includes a fluid-flow junction member into which the second end of each of the conduits is coupled. The second end of the conduits can carry a selected connector such as a luer twist-lock connector or a hollow piercing needle or can be directly inserted into the junction.

A plurality of electrically controlled occluders, one associated with each conduit member, provides for controllably turning the fluid flow from a respective container on and off. The occluders can include a tubing conduit retaining head to prevent inadvertent removal of the conduit. The fluid enters into the junction member and flows into an output conduit. Pumping means are provided to effect the fluid flow and deliver the combined fluid flow at a controllable rate.

The electrically actuated occluders, as well as the pumping means function in conjunction with a programmable control unit. The programmable control unit includes means for storing and executing one or more fluid delivery schedules which can extend over a substantial period of time, such as 24 hours and for controlling the on/off sequencing of the occluders as required by the programmed schedules.

Further, the control unit includes information relating to inter-fluid and drug compatability important in intravenous drug delivery. The compatability between various specified fluids and the drugs compounded into them can be examined prior to activating the scheduled delivery sequences. The control unit also provides control circuitry to actuate pumps to provide the required combination of flow rate and volume delivered at the specified times at the output port.

Each occluder controls the on/off flow of fluid from its assigned fluid container. In operation the system intermittently actuates selected occluders for selected periods of time, so as to provide at the output of the junction a plurality of sequentially delivered fluid quanta from a sequence of fluid containers. This is termed fluid multiplexing. These quanta then intermix while flowing through an output fluid-flow conduit to the fluid port, effectively providing essentially simultaneous delivery of multiple fluids.

By appropriately prolonging the open and close time intervals of selected occluders, the system is capable of delivering the fluid in a scheduled, non-multiplexing, intermittent or continuous mode.

Further, in accordance with the invention, the control unit regulates the actuation or timing of the electrically controlled occluders such that as the fluid administration is subjected to scheduled changes over the course of a predetermined time, the scheduled output flow rate is maintained with respect to the various fluids being provided and any fluid-flow transients due to the schedule changes can be minimized. Transients are minimized by inserting compensation phases into the predetermined delivery schedule.

The electrically energized occluders can be implemented as solenoid actuated clamps. Each clamp has a biasing mechanical return/fluid shut off spring.

The clamp, in response to a first level of applied electrical energy, can move from a first fluid-flow blocking position to a second, fluid flow enabling position. The clamp can be held in the second position at a lower level of electrical energy than was required to get there permitting a flow of fluid through the respective fluid delivery conduit with a low expenditure of electrical energy. The biasing member is available to immediately return the clamp to its first, fluid-flow blocking position, in resonse to the removal of the second level of electrical energy.

Resilient means are provided to resiliently slow and stop the movement of the clamp in response to the applied first level of electrical energy. This provides for quiet operation of the clamp as it moves from a closed position to an open position. On closure, the tubing member cushions the moving portion of the clamp.

A fluid junction is provided, which includes a plurality of fluid input ports. The fluid input ports can be sealed with a luer type connector or a pierceable septum or can be directly connected to the conduit. The pierceable septum has a thickness on the order of 0.25 inches or 7 mm to provide for supporting at least two inserted fluid delivery needles simultaneously as well as for reclosing upon removal of an inserted fluid delivery needle.

The fluid junction provides a completely sealed fluid flow delivery system. In combination with known aseptic techniques, this system can provide a single combined flow of sterile intravenous fluids from a variety of fluid-flow sources to the patient.

The fluid junction can also include an output port to which is coupled the fluid-flow output conduit. A free-end of the fluid flow output conduit in turn can be coupled to the patient.

An additional port can be provided to make possible the coupling of two or more of the fluid junction members together to increase the number of fluid sources that can be used as input sources to the output fluid-flow conduit.

Further, in accordance with the invention a fluid-flow delivery system is provided. The fluid-flow delivery system includes a plurality of flexible fluid-flow delivery conduits forming a tubing set, each with a connector at a first end suitable for coupling to a fluid-flow source, such as a flexible container of sterile intravenous fluid either compounded or not with drugs. At a second end, each of the conduits carries a second coupling member for coupling into or is directly coupled into a fluid junction member.

When coupled together, the sources of fluid, the conduits and the fluid junction member provide a completely closed system in which various sources may be utilized to provide known quantities of selected fluids. These fluids are permitted to pass through the junction member into an output port of the junction member.

Coupled to the output port of the junction member is an output fluid-flow conduit. The output conduit can be of a type which at a free end has a connector couplable to a catheter of a patient. The entire fluid flow delivery system can be formed as a sterile disposable, single-patient delivery system or tubing set. After a predetermined period of time the system would be replaced with another similar, sterile disposable delivery system.

The output fluid flow conduit can be formed with a smaller diameter region, on the order of 0.065", than other tubing members which can have a diameter on the order of a 0.100 inches. This reduced diameter region provides for more precise control of the volumes of delivered fluids.

Further, in accordance with the invention, a method is provided which combines a plurality of fluids from different sources into a continuous, predetermined, composite fluid flow at an output port. The method includes the steps of providing a sequence of known quantities of different fluids, in a predetermined order at a first end of a fluid-flow output member. The method further provides for mixing the various discrete quantities of different fluids in the output member so as to provide at a second end of that member, a continuous fluid-flow having predetermined proportions and at a predetermined rate such that a predetermined volume of each selected fluid is provided at the output port during a selected time interval.

Further, the method provides for checking the compatability of a selected predetermined set of fluids to be provided and any drugs which may be compounded into them to determine that such fluids can be delivered simultaneously without undesired interaction with one another. The combined fluid-flow output can be delivered to the output port at a controlled rate by a pump. Alternately, the combined fluid-flow output can be delivered by means of the force of gravity.

Numerous other advantages and features will become readily apparent from the following detailed description of the invention and the embodiments thereof, from the claims and from the accompanying drawings in which the details of the invention are fully and completely disclosed as part of this specification.

DESCRIPTION OF THE DRAWINGS

FIGS. 1–17 describe the embodiments disclosed closed in parent application Ser. No. 083,843;

FIG. 2 is a perspective view of a multi-fluid delivery system in accordance with the parent application;

FIG. 3 is an over-all block diagram of the fluid flow system of FIG. 2;

FIG. 4 is a schematic diagram of a disposable set usable with the system of FIG. 2;

FIG. 6 is an electronic block diagram of the system of FIG. 2;

FIG. 7 is a detailed block diagram of an occluder electronic interface in the system of FIG. 2;

FIG. 8 is an electro-mechanical diagram of an electrically operated occluder partly in section

FIG. 9B is a graph of voltage applied to an occluder by the drive circuit of FIG. 9A;

FIG. 11C is a graph of fluid flow quanta vs. time illustrating fluid multiplexing in accordance with the parent application;

FIG. 12 is a view in section of a portion of an output tubing member illustrating spatially spaced-apart quanta of several fluids being delivered by the system of FIG. 2;

FIG. 14B is a pair of graphs illustrating the change in concentration in fluids A and B in the tubing member 388 of FIG. 14A as fluid B flows through;

FIG. 16 illustrates the calculated mixing volumes for the systems of FIGS. 14A and 15A during the time intervals when fluids A and B are mixed in tubing members 388 and 90 respectively;

FIG. 17 illustrates an alternate occluder head usable with the computer controlled occluders in accordance with the parent application:

FIGS. 18–27 are directed to embodiments of the present invention;

FIG. 18 is a partial perspective view of an improved multi-fluid delivery system of the present invention;

FIG. 19 is a partial perspective view of the drop sensor and occluder arrays and fluid junction of the present invention;

FIG. 20 is an enlarged partial perspective view of the occluder array and fluid junction of FIG. 19;

FIG. 21 is a schematic diagram of a disposable fluid tubing set for use with the system of FIGS. 2 or 18;

FIG. 22 is a perspective view of the fluid junction of the present invention;

FIG. 23 is a side sectional view of the fluid junction of FIG. 22 taken along the line 23—23 therein;

FIG. 24 is a partial end sectional view of the fluid junction of FIG. 23 taken along the line 24—24 therein;

FIG. 25 is a partial schematic and side sectional view of the fluid junction and disposable fluid tubing of FIG. 21:

FIG. 26 is a perspective view of one occluder of the occluder array of FIG. 19; and FIG. 27 is a side sectional view of the occluder of FIG. 26.

DETAILED DESCRIPTION OF THE PREFERRED EMBODIMENT

Figure 1A:
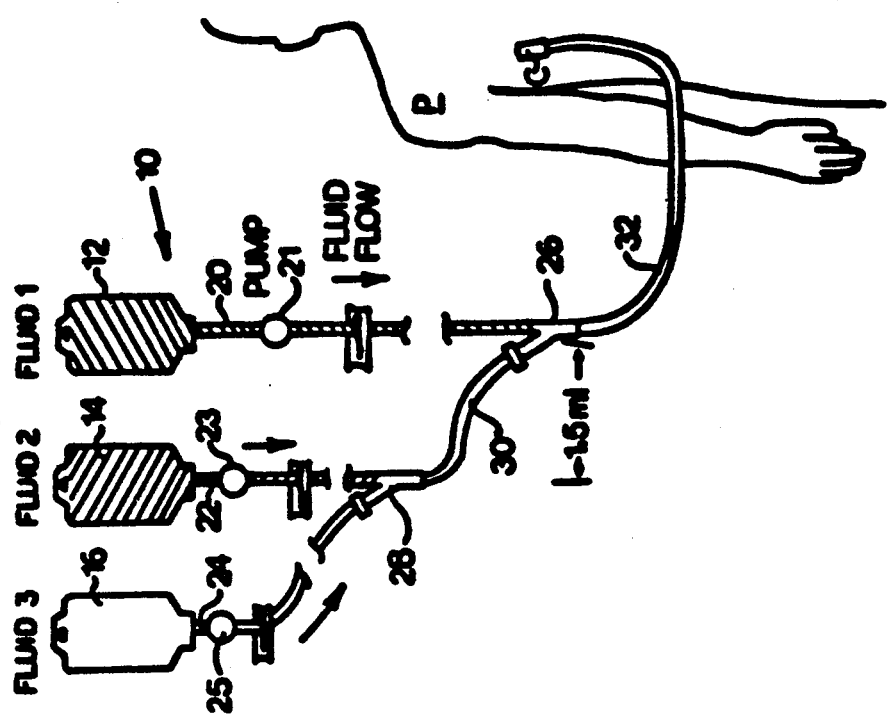
FIG. 1A is a schematic view of a prior art, manually stacked multi-fluid delivery system.

While this invention is susceptible of embodiment in many different forms, there is shown in the drawing and will be described herein in detail specific embodiments thereof with the understanding that the present disclosure is to be considered as an exemplification of the principles of the invention and is not intended to limit the invention to the specific embodiments illustrated.

The embodiments of the parent application are illustrated in FIGS. 1–17.

To assist in the description of the parent application, a prior art three-bag infusion system 10 is illustrated in FIG. 1A. The desired schedule of fluids to be delivered to a patient P is 20 ml/hr of fluid 1, 20 ml/hr of fluid 2 and 50 ml of fluid 3 to be delivered at 100 ml/hr.

The system 10 includes three containers, 12, 14 and 16, each of which contains a predetermined quantity of fluids 1, 2 and 3 respectively. The containers are coupled by flexible fluid-flow conduits, 20, 22 and 24 along with two "Y" connectors, 26 and 28 and an intermediate tubing section 30 to an output fluid-flow conduit 32. Conduit 32 is coupled by a catheter C to the patient P.

Each of the lines 20, 22 and 24 includes an infusion pump 21, 23 and 25 respectively. Each of the pumps 21, 23 and 25 may be adjusted independently.

By way of a typical example, containers 12 and 14 which are sources for fluids 1 and 2 are adjusted and operating so as to supply 20 ml per hour of fluid in each of lines 20, 22 with the result that in line 32, 40 ml per hour of fluid is being provided to the patient. The fluid flow in the line 32 being delivered to the patient P contains equal quantities of each fluid as illustrated in the bottom graph of FIG. 1B at all times less than 30 minutes.

The volume of the line 30 is about 1.5 ml. The volume of the line 32 is about 3.0 ml including the catheter to the patient.

Figure 1B:
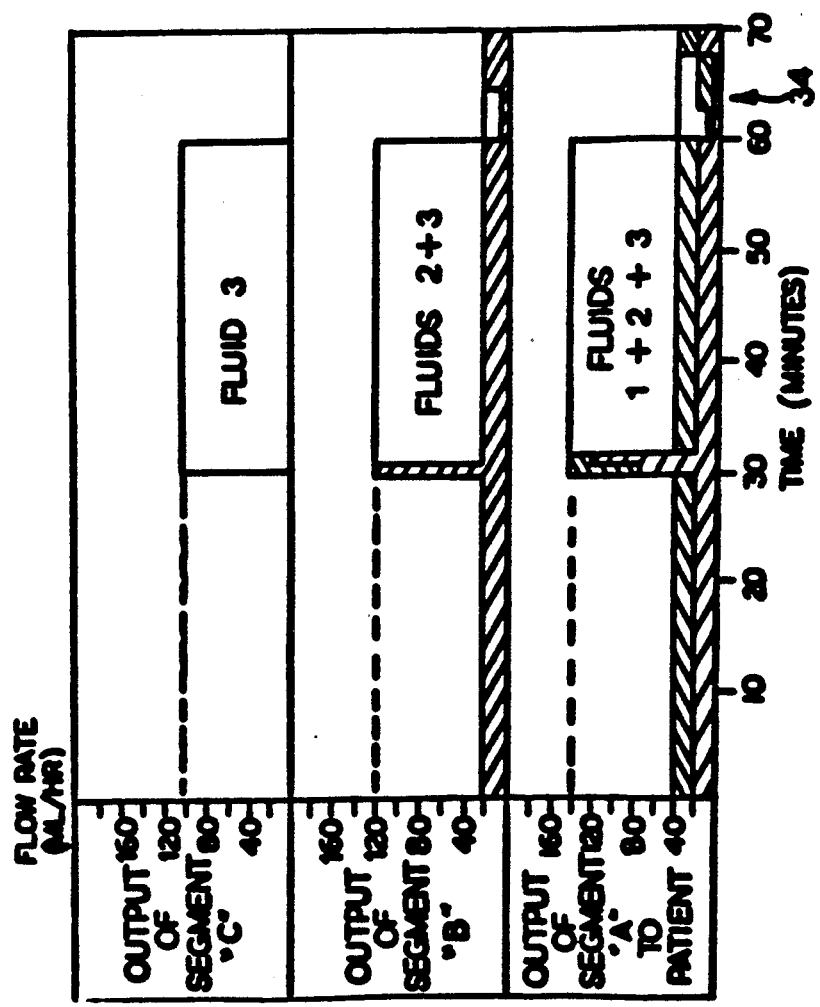
FIG. 1B is a set of graphs of fluid flow vs. time for the delivery system of FIG. 1A.

At the 30 minute point, without changing the flow rates of either tubular member 20 or 22, tubular member 24 is opened and adjusted to a desired steady state flow rate of 100 ml per hour for a period of 30 minutes. The upper graph of FIG. 1B illustrates the flow of fluid 3 in the tubular member 24. However, an investigation of the fluid flow in the tubular member 30 which represents the composite of fluids 2 and 3, as illustrated in the middle graph of FIG. 1B, demonstrates a very unexpected and undesirable change.

Immediately upon initiation of the flow of fluid 3, the rate of flow of fluid 2 in the tubing member 30, which is full of fluid 2, jumps to 120 ml per hour. This rate is six times the desired flow rate of fluid 2. This substantially greater flow rate of fluid 2 continues in the line 30 for approximately 0.75 minute. At that time, the spike of fluid 2 drops and the flow rate of fluid 2 returns to its prior predetermined value of 20 ml per hour. However, it should be noted that depending on the contents of container 14, the fact that fluid 2 has jumped from a desired flow-rate of 20 ml per hour to a flow rate of 120 ml per hour in the line 30 might lead to very undesirable results in the patient's therapy.

Subsequently, at the 60 minute interval, corresponding to the period when fluid 3 is nominally to be completed, container 16 has been emptied of fluid 3. The flow rate of fluid 3 in the line 30 then drops, but not to zero. Instead, as illustrated in the middle graph of FIG. 1B, the flow rate of fluid 3 drops to about 17 ml per hour for about 4.5 minutes. At the end of this period, all of fluid 3 in the line 30 has been drained into line 32. Line 30 is again filled with fluid 2.

The bottom graph of FIG. 1B illustrates the transient fluid flow of the output line 32 to the patient P. At the 30 minute point, when the flow of fluid 3 in the line 24 is initiated, a spike appears in the flow rate of fluid 2 being delivered to the patient P. The flow rate of fluid 2 jumps from the prescribed rate of 20 ml per hour to the patient to approximately 70 ml per hour for about 1.3 minutes. It then jumps to 120 ml per hour for about 0.64 minute.

These two jumps represent respectively over 3 times and about 6 times the prescribed flow rate for fluid 2 being delivered to the patient. In the same two time intervals, fluid 1 jumps from a prescribed flow rate of 20 ml per hour to a flow rate of approximately 70 ml per hour and then drops to a flow rate of approximately 20 ml per hour.

Hence, in the first two minutes that the fluid 3 is being ostensibly administered to the patient, none of fluid 3 has reached the patient P. Instead, a combination of fluids 1 and 2 in the lines 30 and 32 is reaching the patient at flow rates substantially greater than prescribed for those two fluids. For the remainder of the time, until the 60-minute point, fluids 1, 2 and 3 are delivered to the patient at the prescribed and expected rates of 20 ml per hour, 20 ml per hour and 100 ml per hour respectively.

At the 60-minute point the pump 25 has stopped pumping fluid 3 from the container 16. However, a quantity of fluid 3 is still in the process of draining through the tubing members 24, 30 and 32. Immediately after the pump 25 has stopped, the overall flow rate in the line 32 drops to 40 ml per hour.

However, the 40 ml per hour for about a 9 minute time period illustrated in the lower graph of FIG. 1B at region 34 is composed primarily of continuing flow of fluid 3 from lines 30 and 32 with very little flow of fluids 1 and 2. The continuing flow rate of fluid 3 in this time interval is on the order of 28.6 ml per hour. After about 4.5 minutes, the flow rate of fluid 3 drops to about 16.7 ml per hour and continues at 16.7 ml per hour for another 4.5 minutes. It's only after this additional period of time that the fluids 1 and 2 return to the prescribed steady state value.

Hence, the system 10 described above has failed in several significant ways to deliver the desired fluids at the prescribed flow rates. It is believed that the heretofore unsensed and uncompensated for variations in flow rates due to fluid flow transients may be the source of various artifacts and unexplained test results experienced from time to time in the past. For example, if a test were to be conducted, during the time period indicated by the arrow 34, of the effects of fluid 3 on the patient on the assumption that fluid 3 has already been fully provided to the patient P, the test results could be erroneous. This erroneous reading could be due to the fact that fluid 3 is still flowing to the patient during this time interval. In fact, fluid 3 continues flowing to the patient for about 7 to 8 minutes longer than nominally expected.

The fact that fluids 1 and 2, for a $\frac{3}{4}$ minute time interval were delivered at substantially greater rates than prescribed could also lead to erroneous test results.

If an extension set is used between the line 32 and the catheter C, the tubing volume is thereby increased and the above noted problems are exacerbated. If the system 10 is used without the pumps 21, 23 and 25 the results become even less predictable.

Figure 2:
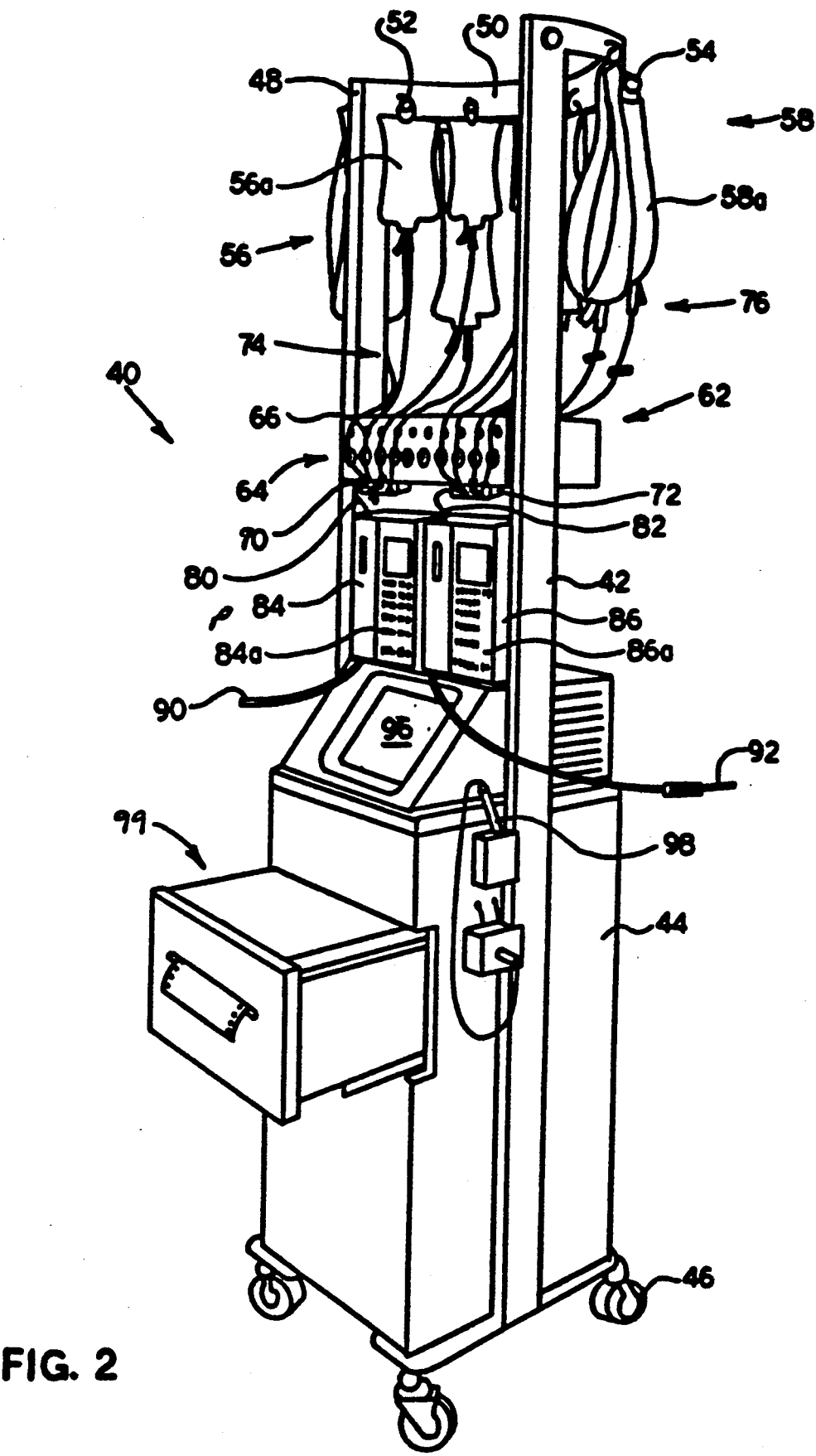

FIG. 2 is a perspective view of a sealed multiple fluid flow delivery system 40 in accordance with the parent application. The system 40 is supported by framework 42 and contained within housing 44. Housing 44 is mounted on a plurality of casters 46 to provide easy movability of the system 40.

At an upper end 48 of the framework 42 is a curved supporting member 50. The member 50 supports a first set of hangers 52 and a second set of hangers 54. The set of hangers 52 and the set of hangers 54 are used for the purpose of hanging flexible solution containers such as the illustrated first plurality of solution containers 56 and the illustrated second plurality of solution containers 58.

The solution container 56a is one member of the plurality of containers 56 which is to be replaced by the second plurality of containers 58 at the end of a predetermined period of time, such as a 24 hour interval. Usually one of the pluralities of containers 56 or 58 at a time is coupled into the system 40. The double set of hangers 52, 54 facilitates hanging the second, replacement, plurality of containers while the first set continues to provide fluid to the patient.

Beneath the containers 56 and 58 is a generally horizontally extending framework 62. The framework 62 supports, in spaced-apart relationship, a plurality of electrically actuated clamps or tubing occluders 64. Each of the members of the plurality of occluders 64 is independently actuatable as is discussed subsequently.

Associated with the plurality of clamps 64 is a plurality of manually operable, lightable actuators 66. One actuator from the plurality of 66 is associated with a corresponding member of the plurality of occluders 64.

Located beneath the member 62 and slidably affixed thereto are first and second fluid junction members 70 and 72. The members 70, 72 can be, but need not be identical.

Linking the solution containers 56 or 58 to the fluid junction members 70 or 72 are a plurality of fluid-flow conduit members 74 and 76. Each of the members of the plurality 74 and the plurality 76 can be formed of flexible medical grade plastic, preferably transparent.

Each of the members of the pluralities 74 and 76 has a first connector, such as a spike connector which can be used to place the conduit in fluid flow communication with a respective fluid-flow container such as 65a, and a second connector at a second end which can be used to place the conduit into fluid-flow communication with the fluid-flow junction 70 or 72.

It will be understood, as described in more detail subsequently, that a sealed fluid-flow system is formed between the plurality of containers 56, the plurality of conduit members 74 and the junction members 70 or 72. Similarly a sealed system is formed with the alternate plurality of fluid-flow containers 58 and the corresponding plurality of fluid-flow conduits 76 and the junction members 70 and 72.

Each junction member 70 and 72 is coupled by an output fluid-flow member 80, 82 respectively to a peristaltic pump 84 and 86. The pumps 84 and 86 are illustrated in FIG. 2 with manually operable control panels 84A and 86A respectively. Such control panels are a convenience but do not form a part of the parent invention. The pumps 84, 86 are precise linear peristaltic pumps with a dead band at the end of each pumping cycle. The type of pump used is not a limitation of the parent invention.

Extending from the pumps 84, 86 are output fluid-flow conduits 90 and 92 respectively. The output conduits 90 and 92 terminate in a luer connector or a piercing cannula and are intended to be coupled directly to a patient's catheter. Such coupling would be in accordance with standard aseptic technique. Upon completion of such coupling, with either the output fluid-flow member 90 or the member 92 or both, a sealed fluid-flow system is formed between the fluid flow sources 56 or 58 and the patient P.

The system 40 also includes a video display 96 for the purpose of displaying status and command information to a system operator or attendant. Information can be input to the system 40 via the display 96 using the light pen or a combined light pen and bar code reader 98 electrically coupled to the system 40.

Also coupled to the system 40 is a hard copy printer 99. The hard copy printer 99 is especially useful for generating hard copy records of regimes of fluids delivered to the patient P for inclusion in the patient's chart or for purposes of auditing the fluid delivery to the patient.

The hard copy printer 99 can be a spooling printer which contains a non-volatile random access memory. The system 40 can spool selected information to the memory of the printer 99. In normal operation, that information need not be printed.

In the event that a preselected condition is detected, that information could then be printed for analysis purposes.

Figure 3:
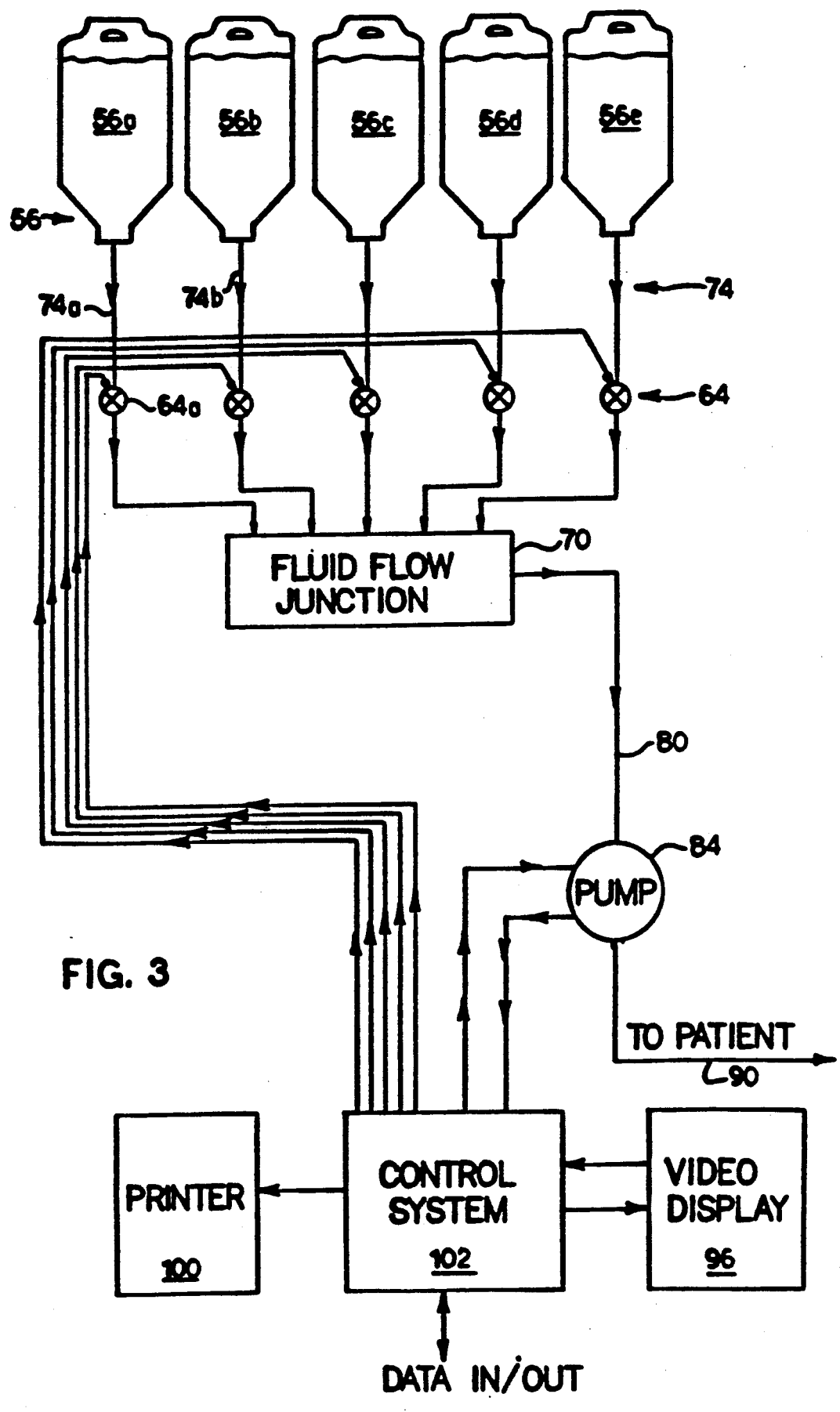

FIG. 3 is an overall block diagram of the sealed fluid-flow circuitry of the system 40. Each of the containers, such as the container 56a is coupled via a corresponding flexible conduit, such as the conduit 74a through a corresponding occluder, such as the occluder 64a to the fluid-flow junction 70.

The output line 80 from the fluid-flow junction 70 passes through the pump 84. Output from the pump 84 via the output fluid-flow conduit 90 is then coupled to the patient.

A control system 102 is electrically coupled to each of the members of the plurality of electrically actuated occluders 64, the pump 84, the video display 96 and the printer 99. The control system 102 includes a Data In/Out port.

Figure 4:
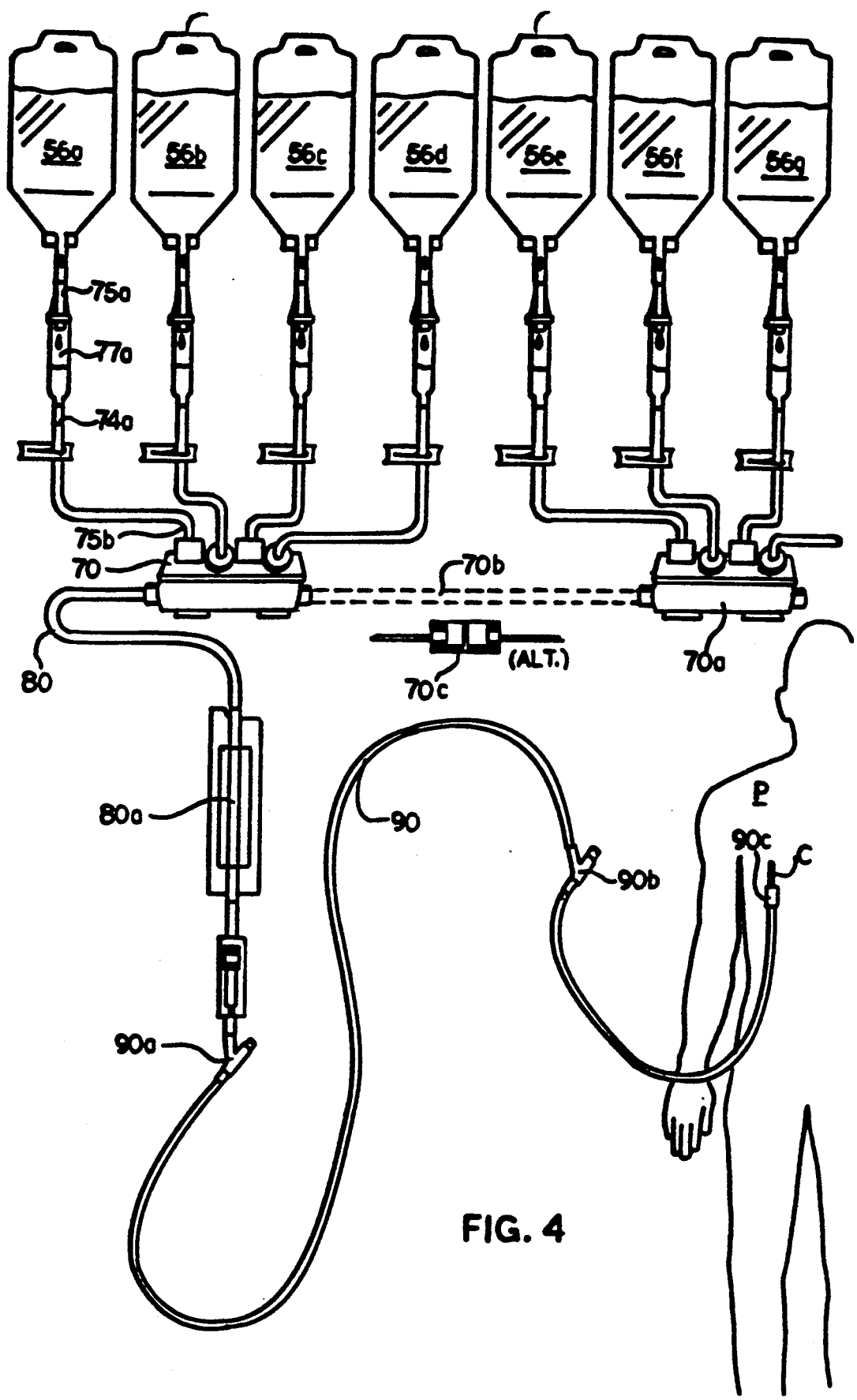

FIG. 4 illustrates in greater detail the fluid-flow circuitry of the system 40. In FIG. 4, container 56a is coupled to the tubing member 74a. The tubing member 74a terminates at a first end in a spike connector 75a. A drip chamber 77a is carried by the tubing member 74a. The spike connector 75a can be used to puncture the access port of the container 56a and as is well-known can also be a sterile connector.

The drip chamber 77a is useful for manually setting a rate of fluid from the container 56a should that be desirable. It is also intended to act as a barrier against air from container 56a entering the tubing member 74a and it is also used as a means to observe that fluid flow from the container 56a takes place. The tubing member 74a terminates at a second end in a connector 75b of a type which can removably and sealably engage the fluid junction member 70. Other containers 56b, 56c or 56d are coupled to the junction member 70 using identical tubing members.

If it is desirable to couple more containers to the fluid junction member 70, as illustrated in FIG. 4, a second fluid junction member 70a can be coupled to the junction member 70. This coupling can be accomplished by means of a tubing member 70b of a selected length or by means of a double-ended cannula 70c. The double-ended cannula 70c can pierceably engage both the junction member 70 and the junction member 70a.

Another way is to have member 70 have its non-tubing end as a pierceable septum and 70a have a cannula as one end. They can then be joined together by piercing the end of 70 with the cannula of 70a. A third way is to put two needles into a single septum. They are designed to accept two needles without leaking. When so coupled together, the containers 56a–56g all drain into a single tubular output conduit Tubular conduit 80 has a region 80a which is designed to be inserted into the pump 84 for the purpose of forcing fluid therethrough at a predetermined rate. Tubing section 90 includes a first "Y" junction 90a which is usable for withdrawing air or any other fluid from the composite output fluid. The output conduit 90 also includes a second "Y" junction 90b for the purpose of injecting additional fluids or medication into the conduit 90 at a site very close to the patient P.

The tubular member 90 has a connection 90c, which can removably engage a main-line catheter C. This type and location of siting on a patient is not a limitation of the parent invention. Catheter C has previously been surgically inserted into the patient P. Since the "Y" connector 90b is located relatively close to the catheter C, additional fluids or medications which are injected via the connector 90b will in a very short period of time be infused into the patient P.

In the fluid flow transfer set of FIG. 4, the tubing member 80 has a nominal diameter on the order of 0.100 inches. The tubing member 90 has a nominal diameter on the order of 0.065 inches. The smaller diameter of the member 90 minimizes the volume of fluid residing in the set between the pump, such as the pump 84 or 86, and the patient P. When flushing the line 90, the smaller diameter means that less flush will be needed.

Figure 5A:
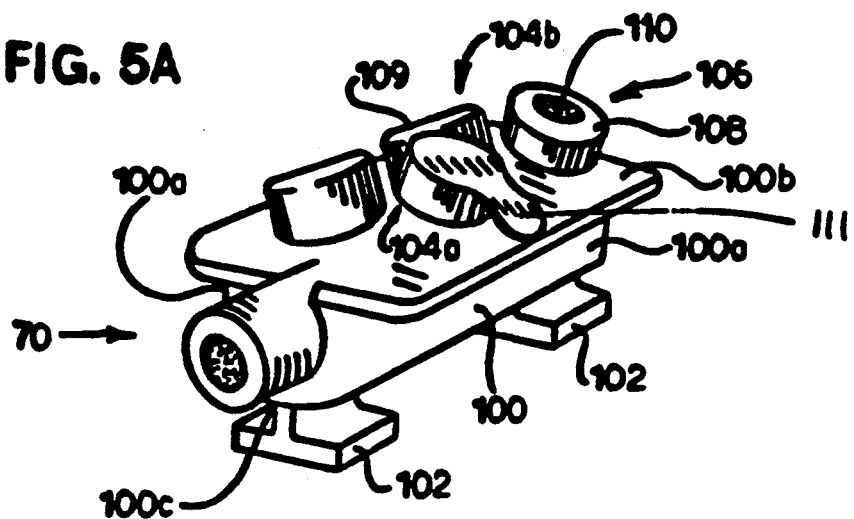
FIGS. 5A–5E illustrate alternate forms of the fluid junction member of the system of FIG. 2.

FIG. 5A is a perspective view of the fluid-flow junction member 70. Junction member 70 includes a housing portion 100 which is formed with spaced apart elongated sides 100a. Sides 100a terminate in a planar shield member 100b. As will become more apparent subsequently, when the elongated side members 100a are being gripped manually, the shield member 100b provides protection to the manually gripping fingers of the attendant.

The elongated side members 100a also terminate at an end surface 100c. Affixed to the surface 100c are mounting members 102. Mounting members 102 slidably engage slots or openings at the base of the panel 62 for the purpose of removably mounting the fluid junction member 70 on the system 40.

Located on the protective shield 100b are a plurality of sealed input ports 104a and 104b. Each of the fluid input ports, such as a typical port 106 is formed with a cylindrical housing 108. The housing 108 extends at an angle from a housing 109 in the plurality 104b.

A pierceable septum 110 is surrounded by the housing 108. The septum 110 is formed of pierceable rubber of a type which is known to reseal itself upon removal of a piercing cannula. The septum 110 provides a continuous sealed region through which sterile fluids may be injected into the junction member 70.

The members of the plurality of access ports 104a are each oriented about an axis of rotation which is at a 45 degree angle to the axis of rotation of members of the plurality of input ports 104b. In addition, the members of the plurality 104a are staggered, and spaced between the members of the plurality 104b.

Each of the ports in the pluralities 104a and 104b can be covered by a removable cap 111. The cap 11 can protect the septum and keep it sterile. Covering the ports provides a continuously sterile septum, such as the septum 110 which need not be wiped with a disinfectant prior to use.

The offset and angular orientation of the ports 104a and 104b is for the purpose of ease of attachment of the conduit members 74 illustrated schematically in FIG. 4.

Figure 5B:
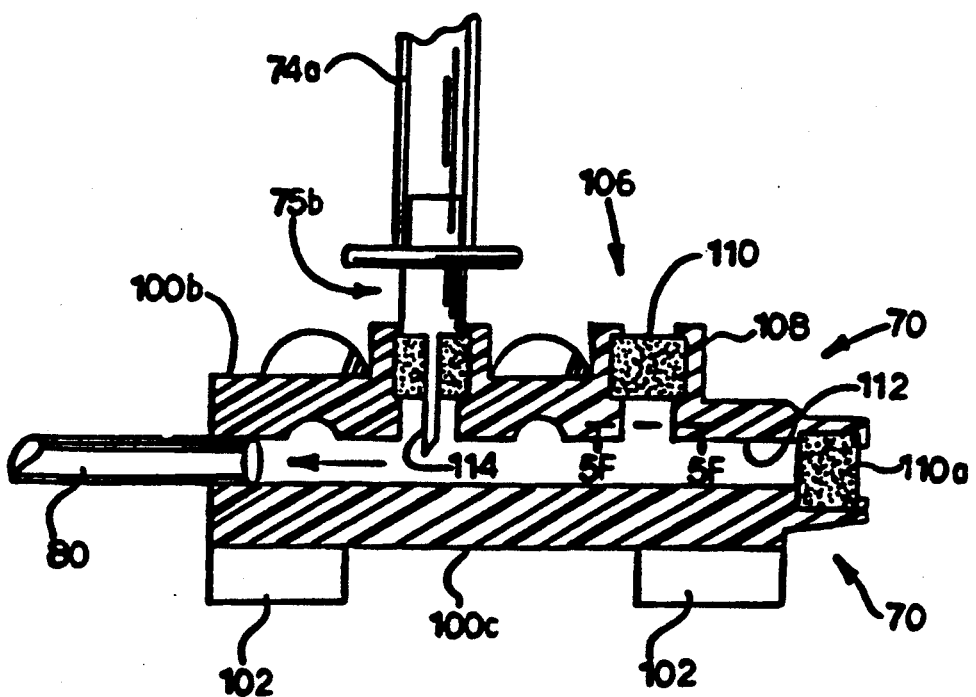

With reference to FIG. 5B, the housing 100, shown in section defines an internal flow path 112 which has a generally circular cross section. A cannula 114 which is affixed to the connector 75b can be inserted through a sterile septum, such as a septum 110 and into the region 112. Fluid can then flow from the container 56a through the tubing member 74a and into the central region 112 of the junction member.

Fluid can then flow from the junction member 70 through the tubing member 80 to the patient. As illustrated in FIG. 5B, the use of the pierceable septum, such as the septum 110 provides for a continuously sealed system for fluid flow between the souce, such as the container 56a and the patient P. Removal of the cannula 114 from the septum 110 closes the junction member 70 as the rubber seals the access port created by the cannula 114.

It should be noted that the fluid junction member 70 is always open for receipt of and flow of fluid therethrough. The junction member 70 does not function as a mixing chamber. Rather, the junction 70 provides only a junction such that a plurality of different fluids from a plurality of solution containers such as 56a–56d can sequentially flow into the output tubing member 80.

In accordance with the parent application, the thickness of each septum, such as the septum 110 is on the order of 0.25 inches. The thick septum provides a wiping action on insertion of the piercing cannula 114 to further block entrance of any contaminating agent into the closed system.

In addition, the thickness of the septum 110 will support 2 or 3 inserted cannuli without tearing or leaking. The added thickness provides that the septum 110 may be pierced more than once in a 24 hour period, and still continue to properly reseal on removal of the piercing cannula.

The shield 100b is especially useful in connection with inserting the cannula 114 into the septum 110 in that the person inserting the cannula can manually grip the housing sides 100a without fear of jabbing himself-/herself with the cannula 114 since a reasonable amount of force is required to insert the cannula through the thick septum 110.

Affixed to an end of the housing 100 is a septum 110a. The septum 110a can be used for the purpose of joining together two junction members such as 70 and 70a illustrated in FIG. 4.

The dimensions of the channel 112 are made as small as possible consistent with fluid flow from the inserted cannuli into the output tubing member 80. As a result, the junction member 70 at any one time contains a very small volume of fluid. This minimizes inter-fluid mixing in the junction member 70.

It will be understood that the channel 112 could be formed with other than a circular cross section. The exact shape of the channel 112 is not a limitation of the parent invention. Further, it will be understood that while the pluralities of injection sites 104a and 104b have each been illustrated in FIG. 5A with an axes of rotation offset from the other to facilitate independent accessability to each site, the exact orientation of the injection sites with respect to one another is also not a limitation of the parent invention.

Figure 5C:
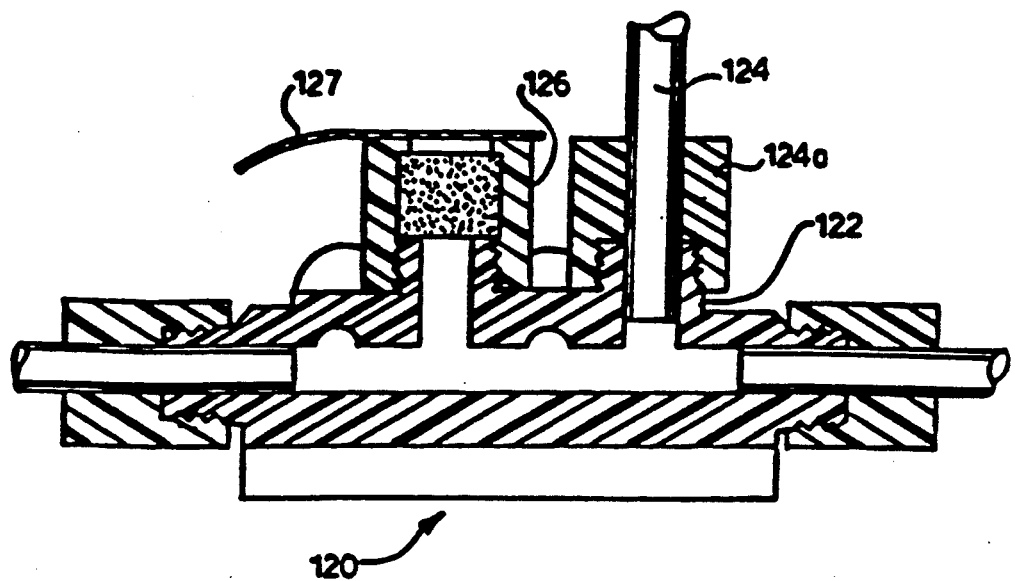

FIG. 5C illustrates an alternate embodiment 120 of the junction member. The junction member 120, in contradistinction to the junction member 70, is formed with luer twistlock connectors 122. Each of the input fluid-flow conduits, such as the conduit 124 carries a matching luer connector member 124a which can engage the member 122 permanently affixed to the junction member 120. It will be understood that prior to coupling the tubing member 124 to the junction member 120, the luer connector 122 would be sealed with a removable luer lock cap.

As an alternate to the luer connector 124a, a luer connector 126 with a septum could be used. In this instance, a tubing member, such as the tubing member 74a with the piercing cannula 114 could be used. The connector 126 could also be sealed with a removable cap 127.

Figure 5D:
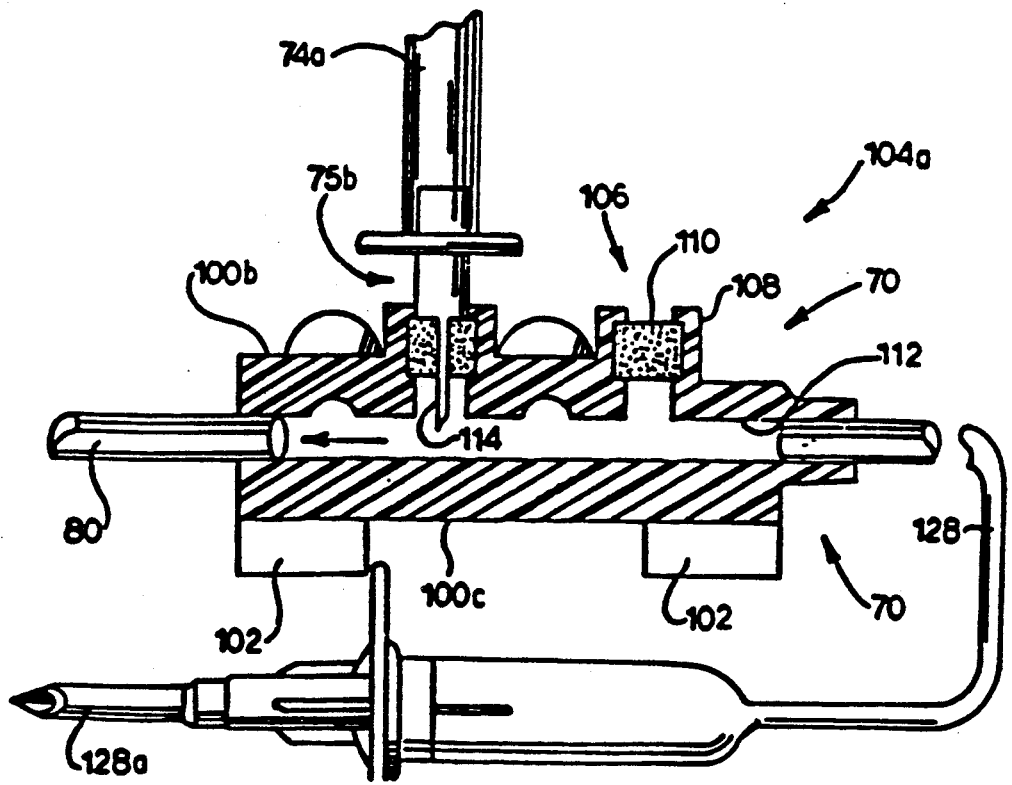

FIG. 5D illustrates yet another variation of the junction 70. A tubing member 128 is coupled to the flow path 112. A free end of the tubing member 128 carries a spike connector 128a. The connector 128a can be used to couple a container of a flush solution to the junction 70.

Figure 5E:
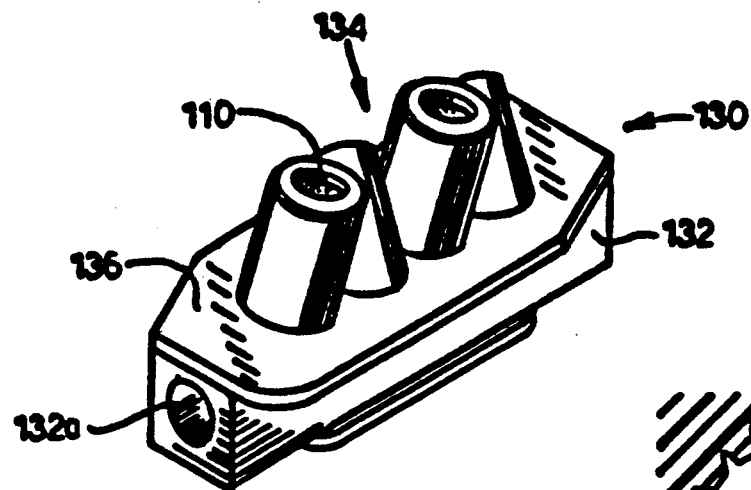

FIG. 5E is a view of yet another junction member 130. The junction 130 has an elongated housing 132 with a flow path 132a therethrough. A plurality of ports 134, with members offset from one another, is also provided. A shield 136 protects the fingers of an operator inserting a cannula into one of the ports 134 and can also be used as a spring like plate to facilitate the mounting of the junction to a hold bracket. The foot member 102a is a continuous member.

Figure 5F:
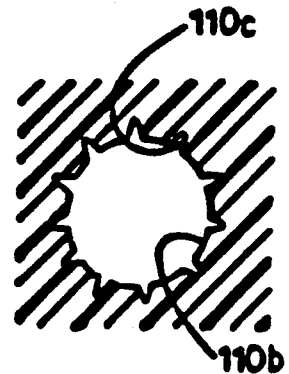
FIG. 5F is a fragmentary, enlarged sectional view taken along plane 5F—5F of FIG. 5B.

As illustrated in FIG. 5F, the input ports 108 can each be formed having a circular cross section 110b. A plurality of capillary spline grooves 110c can be spaced about the periphery of the circular cross section 110b. The grooves 110c provide a means for inflowing fluid to displace the entrapped air in the input ports 108, or prime, when a liquid is initially introduced into the system.

Figure 6:
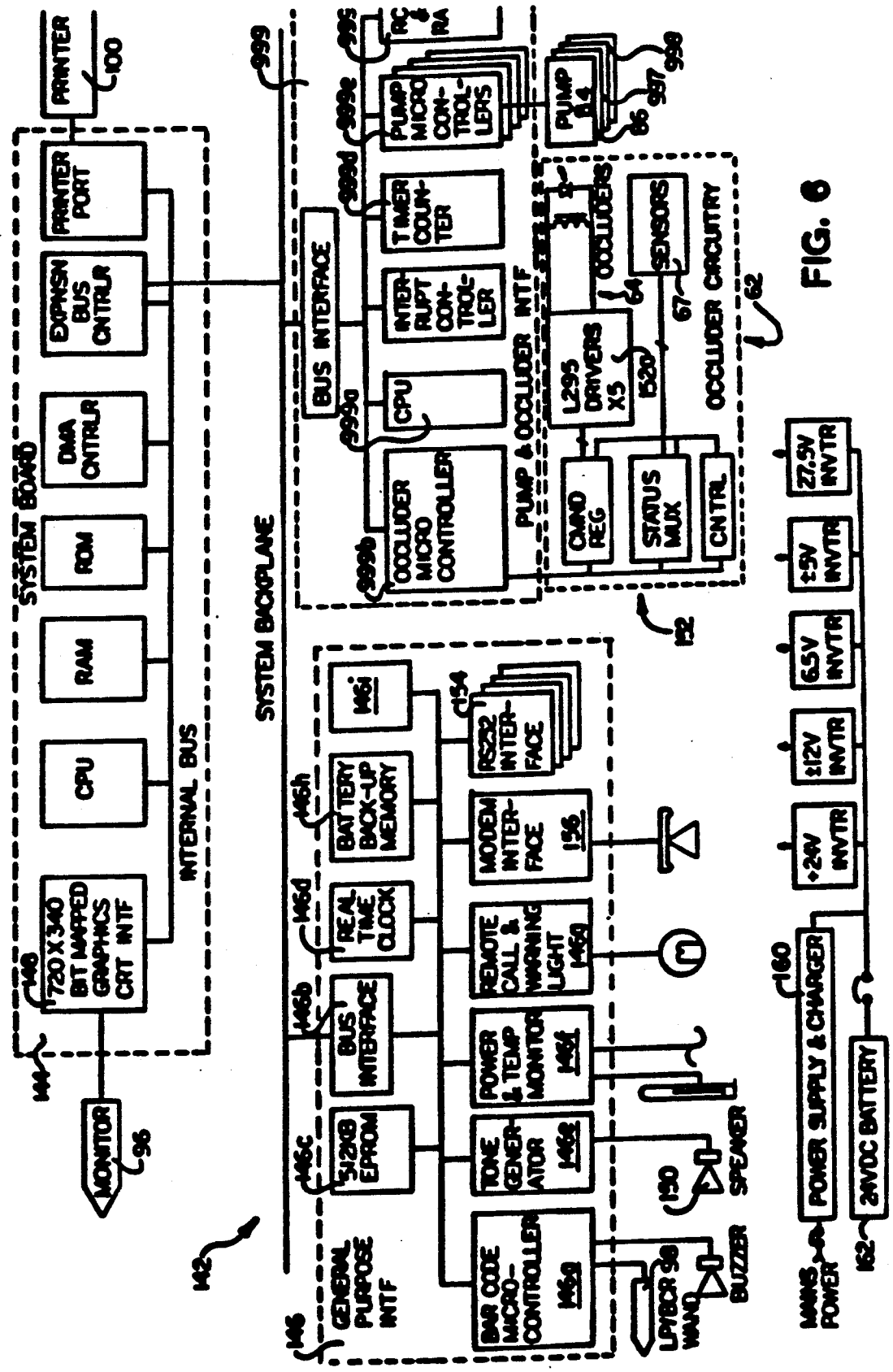

FIG. 6 is a block diagram of a control system 142 usable with the fluid delivery system 40. The control system 142 includes a main processor system board 144. The board 144 includes 80C88 and 80C87 programmable processors. The system board 144 also includes 640 kilobytes of random access memory, 64 kilobytes of read only memory, a graphics controller 148 to drive the monitor 96 and various input-output circuitry. Coupled to the main processor system board 144 is a pump and occluder interface 999.

The interface 999 includes as a secondary processor an 80C88 programmable processor 999a. The interface 999 also includes an occluder or clamp interface 999b along with EPROM and DRAM memory 999c and a timer counter 999d. The pump and occluder interface 999 also includes four microcontrollers 999e which communicate with and control the function of pump 84, pump 86 and two optional remote pumps 997 and 998.

The occluder interface 999b is electrically coupled to occluder drive circuitry 152 which is located adjacent the supporting frame 62. The circuitry 152 includes a plurality of drive circuits, such as the drive circuit 152a. Each drive circuit is associated with a particular occluder such as the occluder 64a.

Each occluder has associated therewith a multielement position sensor 67 which provides feedback via the occluder interface 999b to the processor 999a. The sensors 67 can be switches, photo-optical or other non-contact position sensors such as capacitive or inductive sensors.

A general purpose interface 146 is coupled to the system board 144 through the bus interface 146b to provide input/output capability. Included are a bar code microcontroller 146a and its associated light pen/-bar code reader wand 98; a tone generator 146e and associated audio speaker 150; a power and temperature monitor 146f; a remote nurse call and warning light circuitry 146g; modem interface circuitry 156; a real time clock 146d; 4 Kb RAM battery memory 146h; and a watchdog timer 146i to sense timing error. To provide additional input-output communication facilities, the general purpose interface 146 includes a multi-channel RS232 interface 154.

Power to the system 40 is supplied via a power supply 160 which operates off of standard AC power lines and in turn charges a 24 volt battery 162 to permit the unit 40 to continue operating when being moved from one location to another. A typical battery could be an Eagle Picher CFM24V25AH. Power supply voltages available to the system 40 include ±5V, +6.5V, ±12V, +24V, +27.5V.

Figure 7:
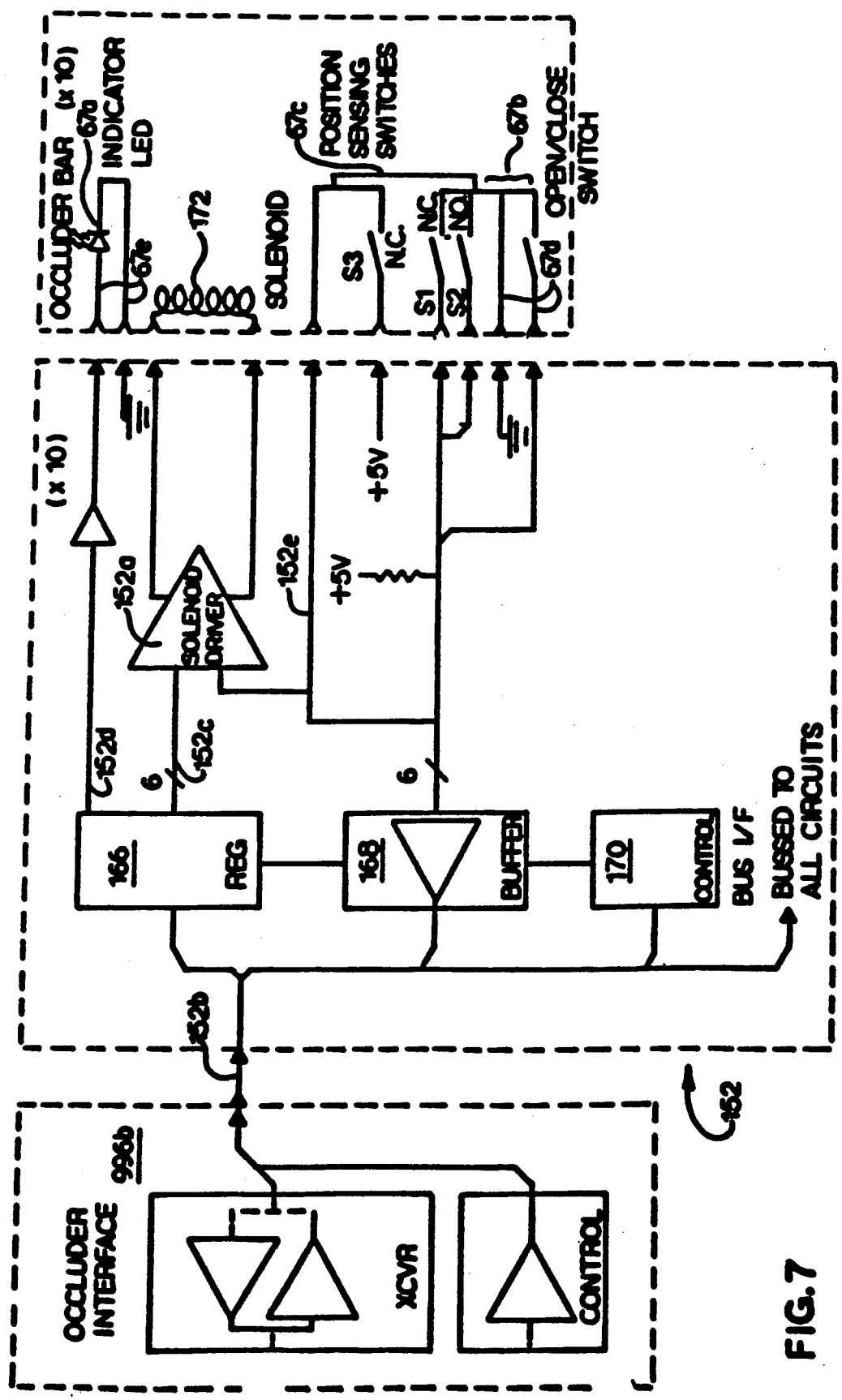

FIG. 7 is a block diagram schematic of the interface circuitry 152 associated with each of the occluders 64. The interface circuitry 152 includes, for each occluder, a command or output register 166, a feedback buffer 168 and control circuits 170. Data and signals are transmitted between the occluder interface 999b and the interface circuitry 152 via a communication bus 152b.

The occluder driver 152a is actuated by setting a bit in the command register 166. The set bit on a line 152c, provides an input signal to the driver 152a. Output from the driver 152a powers a solenoid coil 172 to open the corresponding occluder.

Another bit in the output register 166 can be set to turn the occluder indicator 67a on and off. The set bit on a line 152d and an associated buffer drive power the indicator 67a. The indicator 67a can be continuously on or can blink if desired.

Feedback inputs to the interface circuitry 152 include the manual solenoid override switch 67b and a three position, multi-pole sensing switch 67c. Depression of the switch 67b can cause the occluder 64a to be energized for removal or insertion of a section of tubing.

The three position sensing switch 67c provides feedback to the interface as to the status of the occluder. Pole S1 is normally closed when the occluder is in its closed or unenergized position. Pole S2 is normally open and closes in an intermediate condition of the occluder. Pole S3 is normally closed indicates on opening that the occluder is fully energized and open permitting fluid flow.

The solenoid driver 152a applies a suitably high voltage and current so as to magnetize the airgap present when the occluder plunger is in its first or closed position. When the plunger has moved to its second or open position permitting fluid flow, which takes about 25 milliseconds, the voltage and current to the coil 172 is reduced. This second level of electrical energy is sufficient to maintain the occluder in its second or fluid flow permitting position, but yet minimizes heating of the coil 172 and minimizes drain from the battery 162.

When the coil 172 is deenergized, a coil spring pushes the occluder 64a to the closed position with a force on the order of 2-3 pounds. The initial voltage applied by the driver 152a is on the order of 16 volts.

Figure 8:
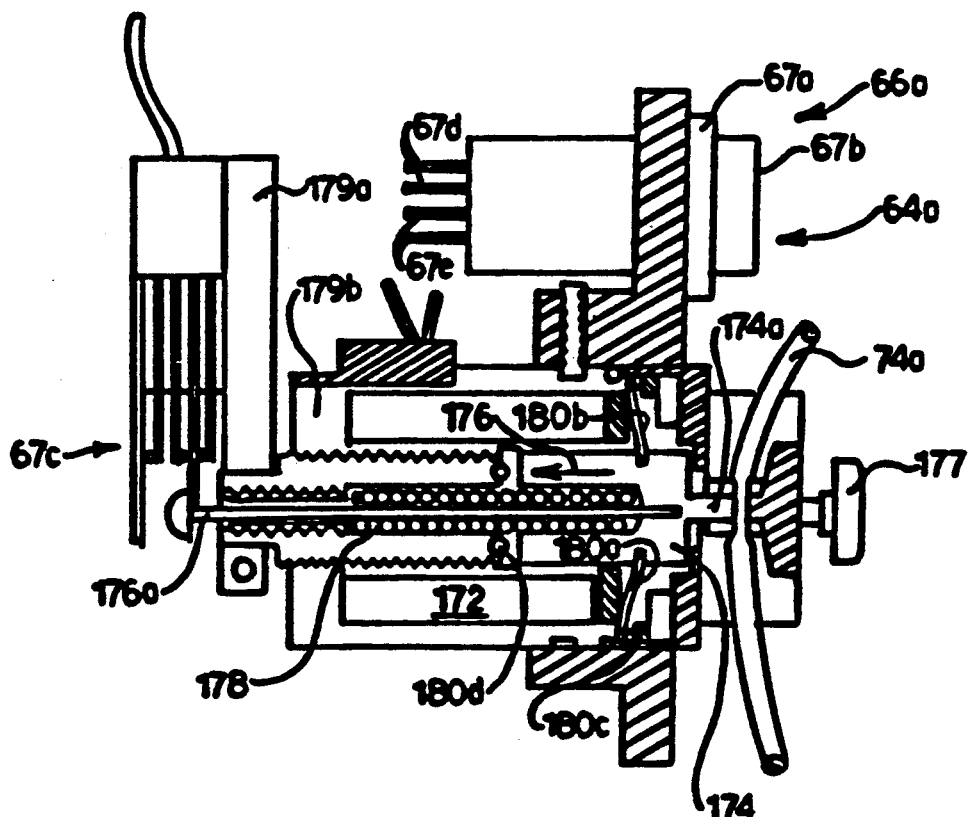

FIG. 8 illustrates the structure of the electrically actuated occluder 64a. The other occluders have an identical structure. Occluder 64a includes the electrically energizable solenoid coil 172 which surrounds a movable plunger 174. The plunger 174 is movable in a direction 176 under the influence of the magnetic field generated by the coil 172 from a first, fluid flow blocking position to a second fluid flow enabling position illustrated in FIG. 8.

A tubing clamping member 174a is carried by the plunger 174. When the occluder is not energized, the clamping member 174a blocks fluid flow through the inserted tubing member 74a. An actuating rod 176a also carried by the plunger 174 opens and closes switch contacts S1, S2 and S3 as the plunger moves.

A biasing spring 178 forces the plunger 174 to return to its first position upon removal of electrical energy from the coil 172. A manually depressable knob 177 is provided to manually move the plunger 174 away from the tubing 74a.

The position sensor 67c is carried by a bracket 179a which is supported by the top pole of the solenoid 172. The position sensor 67c is implemented as a three contact mechanical switch assembly. The three contacts S1, S2 and S3 provide position information to the circuitry 152 for various possible positions of the clamping member or plunger 174. The first position corresponds to the occluder 64a being deenergized without any tubing having been inserted. In this condition S1 and S3 are closed and S2 is open. The second position corresponds to the position illustrated in FIG. 8 with the plunger 174 moved to its fully open position permitting fluid to flow through the tubing member 74a. In this condition S1 and S3 are open and S2 is closed.

The third position is a test position which is intermediate between the first two positions indicating that the plunger 174 is stuck part of the way between its first or fully closed position and its second open position, as illustrated in FIG. 8. This indicates that the plunger 176 is not in the desired open or closed position. Here S1 is open and S2 and S3 are closed. The presence of tubing 74a in the occluder is indicated if S1 and S2 are open but S3 is closed.

The occluder 64a also includes a plurality of fluid resistant seals. Diaphragm seal 180a, 180b, an annular seal and band compression and O ring seals 180c block incident fluids from entering the occluder and its associated electrical and electronic components housed in the framework 62.

An elastomeric pad 180d provides sound muffling on opening when the plunger 174 moves in the direction 176. The tubing member 74a cushions the plunger 174 on closure.

Figure 9A:
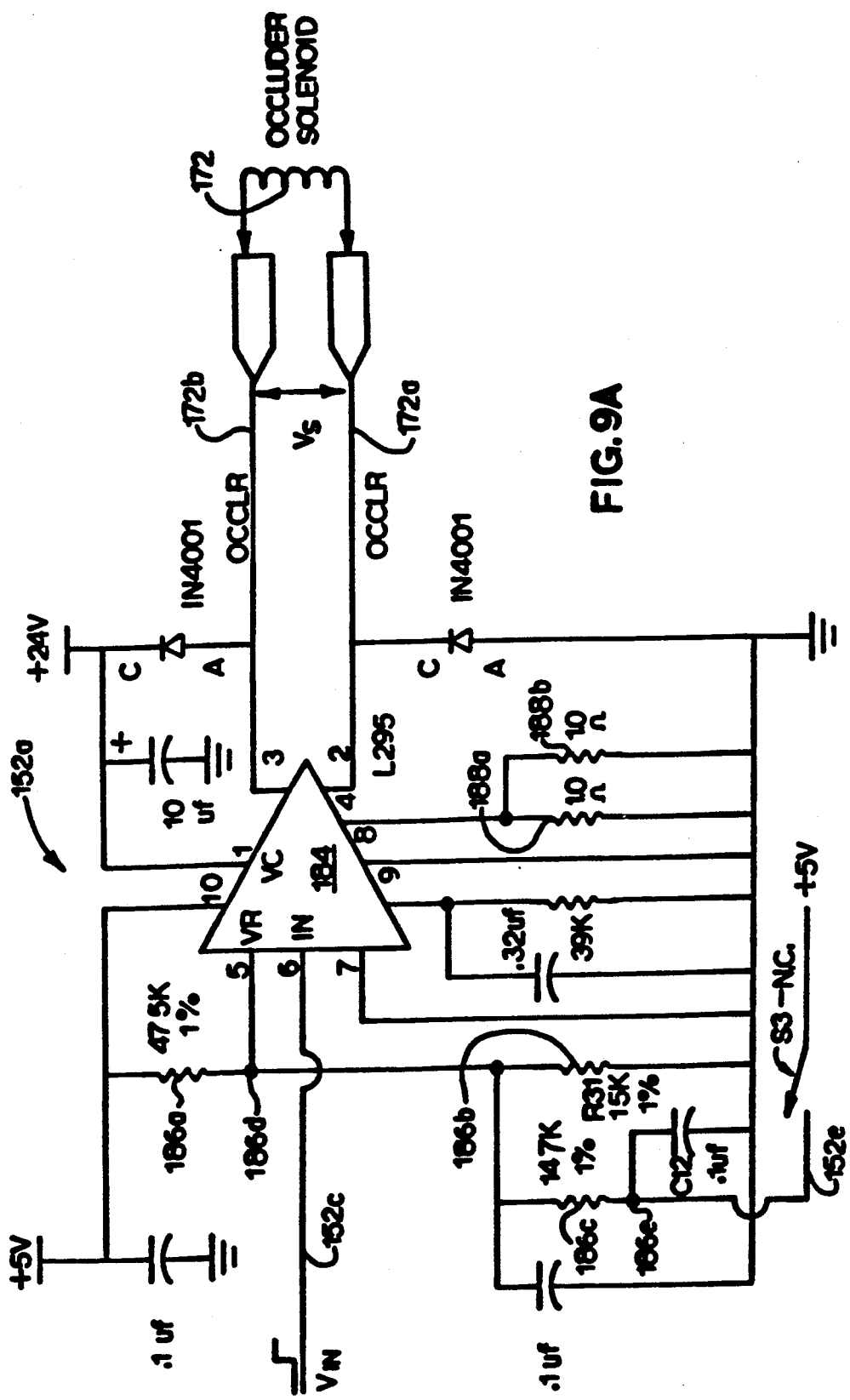
FIG. 9A is a schematic diagram of an electronic drive circuit for use with the occluder of FIG. 8.

With respect to FIG. 9A, the solenoid drive circuit 152a includes an integrated drive circuit 184 which could be implemented as a L295 integrated circuit manufactured by SGS-Semiconductor Corporation. Outputs from the drive circuit 184 via lines 172a and 172b are coupled to the solenoid coil 172. The drive circuit 152 a is typical of those in the system 40. Each drive circuit is associated with a different occluder.

Input to the drive circuit 184 on the line 152c is a five volt or ground signal. The drive circuit 152a energizes the solenoid coil 172 when the input signal on the line 152c is on the order of five volts.

Voltage divider resistors 186a, 186b and 186c are connected at a node 186d to form a reference voltage input at pin five of the circuit 184. At a node 186e the normally closed contact S3 provides a return path to plus five volts except when the plunger 174 has moved to its fully open position.

A parallel resistor combination including resistors 188a and 188b forms a 0.5 ohm current sensing resistor which is in series with the load.

The drive current to the solenoid coil 172 is set by the value of the voltage at the node 186d of the drive circuit 184. With the parallel resistor values 188a and 188b set to provide 0.5 ohm to ground, the circuit 184 is calibrated to provide 2 amps of current to the coil 172 for each one volt of input at the node 186d.

The indicated values of the resistors 186a, 186b and 186c are chosen to provide 0.6 volts at the node 186d. The drive circuit 184 supplies 1.2 amps of pull-in current to the solenoid coil 172 until the plunger 174 reaches its fully open position and opens the switch contact S3. When S3 opens, the voltage at the node 186d is set by the combination of 186a, 186b and 186c and is reduced to 0.2 volts. The driver circuit 184 then supplies 0.4 amps of holding current to minimize power consumption.

In FIG. 9B, a graph of voltage across the solenoid 72 versus time is plotted for a 13.5 ohm solenoid coil. In this case only 16.2V of the available 24V supply is applied by the drive circuit 184. The pull-in and holding currents can be adjusted by changing the values of the resistors 186a, 186b, 186c as well as the sensing resistors 188a and 188b. In the graph of FIG. 9B, the indicated time $t_o$ corresponds to the time when the switch contact S3 opens. At that time power to the solenoid coil 172 is reduced from a pull-in value to a holding value.

Figure 10A:
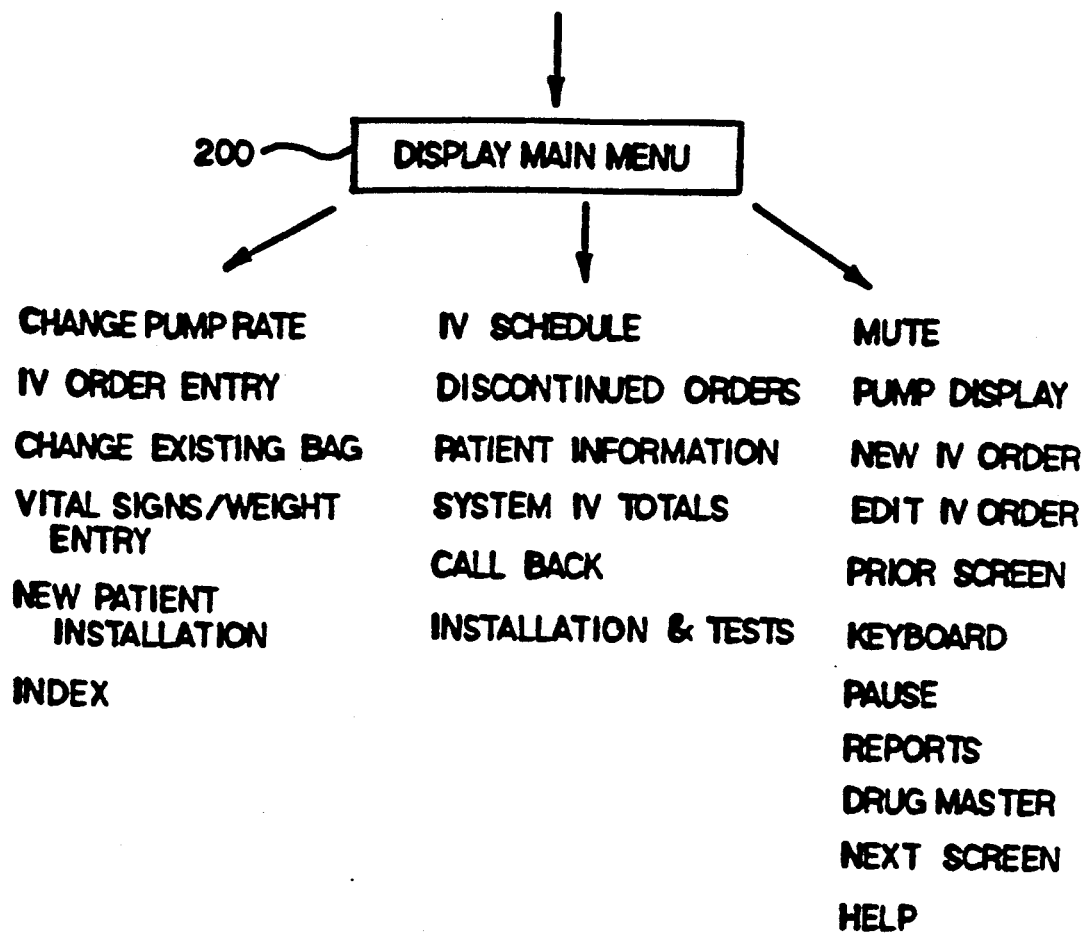
FIG. 10A–10C taken together are a flow diagram illustrating the specification of a plurality of drugs or solutions to be infused by the system of FIG. 2.
Figure 10B:
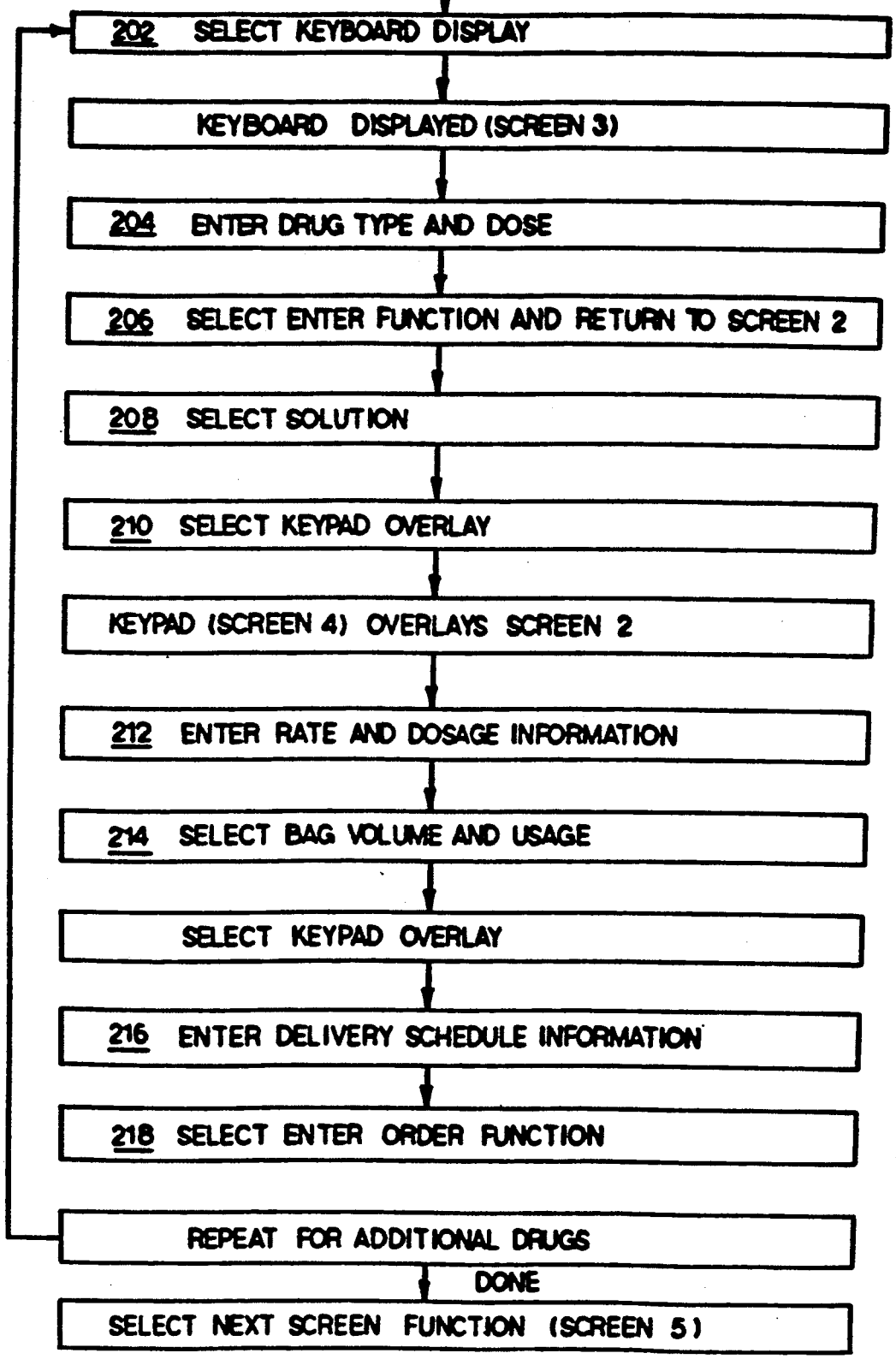
Figure 10C:
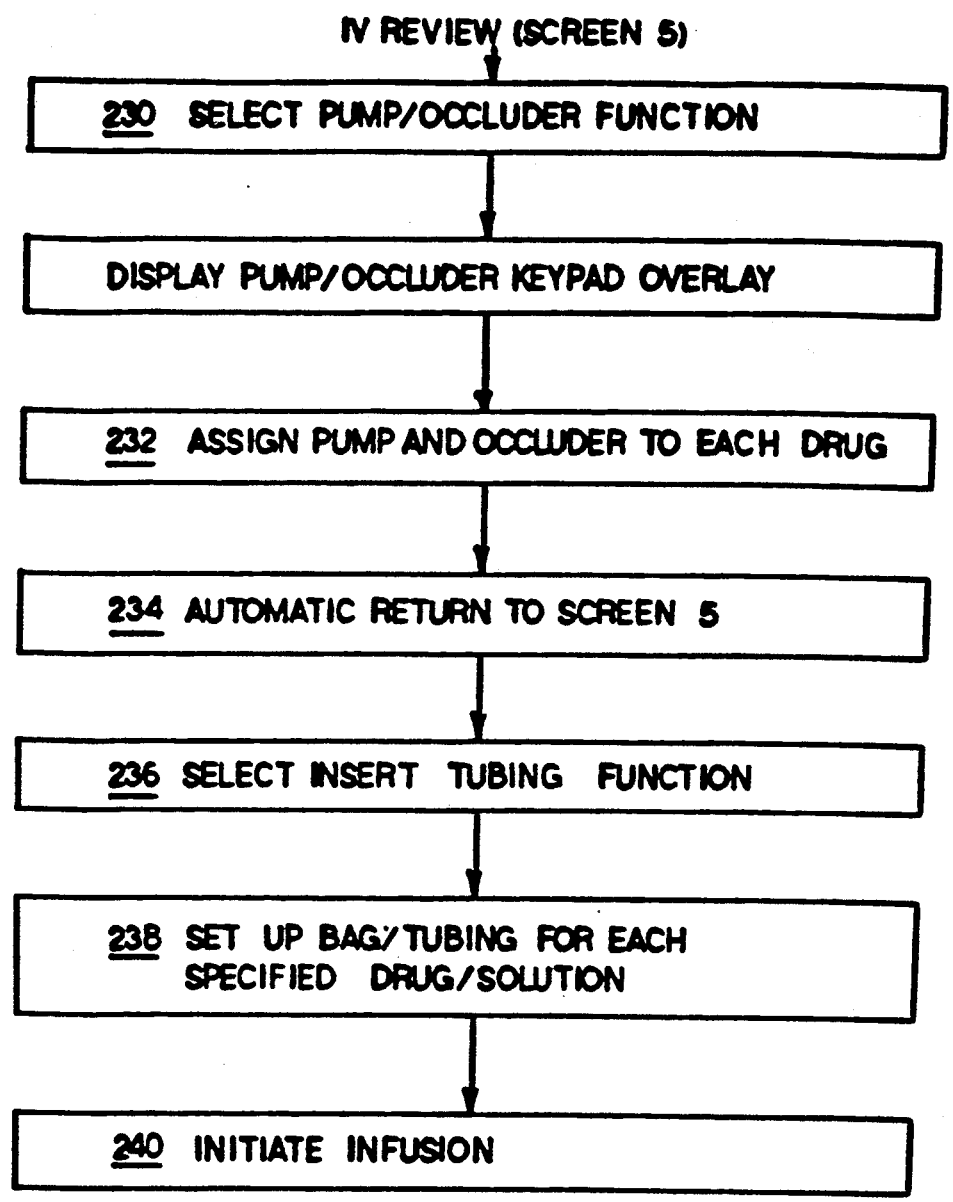

FIGS. 10A-10C together form a flow diagram illustrating representative operator initiatable functions or actions which can be undertaken in connection with the system 40. As illustrated in FIG. 10A in a step 200, a Main Menu can be displayed on the display unit 96. Prior to displaying the Main Menu, if desired. a menu could be displayed for the purpose of calibrating the light pen 98. Operator displayable screens are included herein in an attached Addendum.

The Main Menu is illustrated on Screen 1. For reference purposes, line members are printed along the left side of the screen. At the top of Screen 1, on line 2 a patient's name and identification number (previously entered) as well as date and time can be displayed. On line 4 previously selected pump A or pump B, corresponding to pump S4 and pump 86 can be displayed in combination with previously selected occluder as well as a fluid delivery rate.

Between lines 7 and 19 of Screen 1, members of a plurality of operator selectable actions are identified. For example, with respect to line 7 on Screen 1, the operator can select a change of pump rate. Alternately the operator on line 7 could choose to ask for the IV schedule.

With respect to line 9, the operator can invoke the procedures for IV order entry or call for the list of discontinued orders.

On line 11, the operator can invoke the procedure to change the existing bag or ask for patient information.

On line 15, the operator can invoke the procedure for vital signs/weight entry or, ask for system IV (volume) totals.

On line 17 the operator can invoke the procedures for new patient installation or, ask for a list of call back messages.

On line 19 of Screen 1, the operator can ask for an index of screens and procedures, or, invoke the procedures for system installations and tests.

On lines 22 and 24 of the Main Menu a variety of standard functions is provided which can be selected by the operator. For example, on line 22 the operator can select to MUTE the system alarm. Additionally, the operator can select to view system PUMP DISPLAY, to EDIT IV ORDERS scheduled previously or to display a KEYBOARD overlay.

On line 24, the operator can implement a PAUSE function, a selection of drug specification through the DRUG MASTER screen sequence, or can request a HELP screen. Specification of an action or a function is carried out by the operator using the light pen 98.

It will be understood that while the screens illustrated herein are in a form suitable for printing as textual information that the invention is not limited to such screen formats. For example, various selectable actions or functions can be displayed in reverse video should that be deemed to facilitate operator interaction. In addition it will be understood that if desired a selected function or indicia of action could be caused to blink, before or after selection, to provide visual feedback to the operator of what has been selected.

For exemplary purposes, assuming that the operator selected the NEW IV ORDER function, line 22 of Screen 1, the system 40 would immediately display Screen 2. FIG. 10B illustrates a sequence of steps associated with this function.

Line 2 of Screen 2 again displays the patient's name and identification number. Lines 22 and 24 display the same set of functions as were previously displayed on those lines on Screen 1. On line 4 of Screen 2 the same pump, occluder and rate information is again displayed as was displayed on line 4 of Screen 1.

Line 7 of Screen 2 indicates specification of a drug/dose. The drug potassium chloride with a dose of 20 MEQ has previously been entered. When Screen 2 first appears, the "DRUG/DOSE" identifier can be displayed in blinking form to indicate the first entry. The operator can carry out a drug/dose entry by first selecting a displayable keyboard. This is accomplished by selecting the keyboard function on line 22 in a step 202. When so selected, a keyboard screen, Screen 3 appears on the display 96.

Drug names can be entered using the alphabetical portion of the keyboard on Screen 3 in lines 10-14. The light pen is used for selection of each character in a step 204. The operator selects a sequence of alphabetical characters, each of which appears on line 8 of Screen 3 after it has been selected. In addition, a numeric drug dose can be selected from the keypad at the right side of the keyboard screen in units assigned from the units indicated on lines 18 and 20 of Screen 3.

After a drug and dosage have been entered, the operator in a step 206 then selects the ENTER function on line 17 of Screen 3 using the light pen 98. Upon sensing a selection of the RETURN function, the system 40 then returns to Screen 2 with the entered drug and dosage information displayed on lines 7-9.

The operator in a step 208 can then select one of a group of standard solutions from line 10 of Screen 2. To assist the operator, the "SOLUTION" designator can also blink. After a solution has been selected, the "RATE" designator can be caused to blink by the system 40.

The operator can then in a step 210 specify the KEYPAD function from line 20 of Screen 2. A keypad overlay, illustrated in Screen 4, is then displayed on the right hand side of display 96. Numeric rate of delivery information on line 10 of Screen 2 and dosage volume information on line 13 of Screen 2 can be entered in a step 212. In addition, the operator can enter, with respect to line 13 of Screen 2, the total number of doses to be administered.

The operator can then select in a step 214 one of a group of standard container or bag volumes from line 12 and can specify type of usage from line 14. Types of usage can include intermittent, INTER; continuous, CONT; flushing, FLUSH; keep vein open, KVO; or a combined flush/keep vein open function, FLUSH/KVO.

Again with respect to Screen 2, the operator in a step 216 can then enter scheduling information on line 16 to specify how often the drug or solution is to be provided. Completion of the order is indicated by the operator selecting the ENTER ORDER function in a step 218 on line 20.

Should it be desirable at this time to enter and schedule an additional drug or solution the operator would repeat the above described process again using Screen 2. Once all of the desired drugs or solutions have been specified the operator can in a step 220 specify the NEXT SCREEN function from line 24. This will then cause the system 40 to display Screen 5, the IV Fluid Review and Edit Screen.

On Screen 5, lines 7, 8 and 9, three entered drug types and dosages are displayed. To the right of the displayed drugs is an assigned pump column labeled "P" and an assigned occluder column labeled "OC". FIG. 10C illustrates the steps associated with using this Screen 5.

Each of the drugs has been assigned as illustrated on Screen 5 to the same pump A which can be either pump 84 or pump 86. Each of the drugs has been assigned to a different occluder.

Assignment of pumps and occluders to previously entered drugs can be carried out by the operator. The operator requests in a step 230 a PUMP/OCCLUDER function located on the right end of line 7. When the system 40 senses this request, Screen 6 a keypad for pump and occluder selection is displayed overlaying the right side of Screen 5.

The first drug, on line 7 of Screen 5, can be highlighted for example in reverse video. Using the pump and occluder keypad overlay, a pump can be assigned to that drug along with an occluder in a step 232. Using the SCROLL function, line 20 on Screen 5, each of the drugs on lines 8, 9 can be selected in turn. In a similar fashion each of the drugs displayed on lines 8 and 9 can then be assigned to a pump and an occluder.

The system in a step 234 will automatically suppress the pump and occluder keypad overlay screen after selections are complete. To initiate infusing, the operator in a step 236 can then select the INSERT TUBING function on line 9 of Screen 5.

Subsequent to the system 40 sensing that the INSERT TUBING function has been selected, one of the occluder indicators, such as the indicator 67a, which corresponds to occluder 64a will start to flash. This alerts the operator to insert the tubing for the selected drug or solution into that occluder. This can be accomplished by the operator depressing the OCCLUDER OPEN/CLOSE switch, such as the switch 67d. The system 40 will then energize the corresponding occluder, such as the occluder 64a, which will permit insertion of the tubing associated with the selected solution container into the occluder.

Depressing the OCCLUDER OPEN/CLOSE switch, the switch 67d, a second time notifies the system 40 that the tubing has been positioned in the occluder and the occluder can then deenergize. Each of the remaining occluders can be activated and loaded with a corresponding tubing member in a similar fashion. At this time infusion of the scheduled drugs can be initiated.

In the event that the operator wishes to check interfluid compatibility of those fluids and drugs listed on Screen 5, prior to initiating infusion it is only necessary to select t he COMPATIBILITY function from line 19 of Screen 5.

The system 40 will then display a Compatibility Summary, with respect to the three drugs previously listed on Screen 5, as illustrated by Screen 7. In the Compatibility Summary of Screen 7, the three previously entered drugs are listed on lines 7, 8 and 9.

Near the center of Screen 7, each of the drugs, identified as drug 1, drug 2 or drug 3, is compared to each of the other two drugs. For example, as indicated on line 7, potassium chloride, drug 1, when compared with Tobramycin, drug 2, results in an indicia "C" being displayed. The indicia "C" indicates that those two drugs are compatible. On the other hand, a comparison of potassium chloride, drug 1 with Flagyl, drug 3, indicates an incompatibility.

In order to deal with the incompatibility between the potassium chloride and the Flagyl, the potassium chloride can be assigned to one of the two pumps and the Flagyl can be assigned to the other of the two pumps. This multipump assignment is illustrated near the right side of Screen 7 in a column with a heading "P". To facilitate pump assignment and occluder assignment a pump occluder keypad is displayed along the right side of Screen 7.

It should also be noted in Screen 7 that a FLUSH function is provided on line 20. A flush can be provided both before and after delivery of any selected drug or fluid.

With respect to the Compatibility Summary of Screen 7 it will be understood that drug or solution compatibility or incompatibility information can be prestored in the non-volatile memory 146c. That memory can be updated or its contents modified from time to time depending on the solutions or drugs being used with the system 40. A blank column indicates a lack of information.

Subsequent to initiating infusion, a Medication Summary, Screen 8 can be displayed. Screen 8 provides an identification of scheduled drugs, for example on lines 7, 8 and 9. Additionally, Screen 8 identifies the assigned pumps and occluders along with an indication of scheduled frequency of delivery of the drug or solution. In the right hand portion of Screen 8 a representation of time intervals of delivered drugs during a twenty-four hour period is displayed with quarter hour increments.

The SCROLL functions can be used to move the display through the complete 24 hour time period.

If a hard copy of the Medication Summary is desired, on line 20 an operator can select a PRINT SUMMARY function which causes the system 40 to then create a hard copy of the summary.

It is also possible for an operator to display in various alternate forms the status of scheduled solutions being infused to the patient P. For example, the system 40 provides a Drug Status Display, Screen 9.

In Screen 9 an example of a different set of drugs is identified along with its related solution. For example, on lines 8 and 9 dopamine and dextrose have been identified as being delivered via occluder 4. Further to the right on lines 8 and 9, a delivery rate is specified as well as a total previously infused volume and a remaining volume yet to be infused. Comparable information is provided for drugs and solutions associated with each of the other occluders, such as occluders 5, 6 and 7 which are associated with the same pump.

The system 40 can also assist a health care provider in fluid management. In this regard, Screen 11 provides for forecasting of expected intake volumes of fluids. Line 7 of Screen 11 provides for entry of a maximum fluid volume over a 24 hour period.

Between lines 9 and 18 a display is provided of currently committed fluid quantities, based on 8 hour time periods. Additionally, a display is provided of currently available quantities of fluids which can be added to those quantities already committed during each 8 hour time period. Hence, Screen 11 provides 8 hour projections as well as daily totals with respect to both volumes of committed fluids and currently available volumes of fluids.

In the prior discussion, the system 40 could be operated in a mode wherein one solution at a time was to be infused into the patient P. For example, with respect to Screen 5, potassium chloride was to be infused continuously. Tobramycin was to be infused intermittently. During the time that Tobramycin was being infused, via occluder 2 the potassium chloride would be blocked from flowing via occluder 1.

In an alternate mode of operation, two or more fluids and drugs could be simultaneously infused into the patient P. In the prior art, simultaneous infusion of multiple drugs utilized systems of the type illustrated in FIG. 1A with results of the type illustrated in FIG. 1B.

Figure 11A:
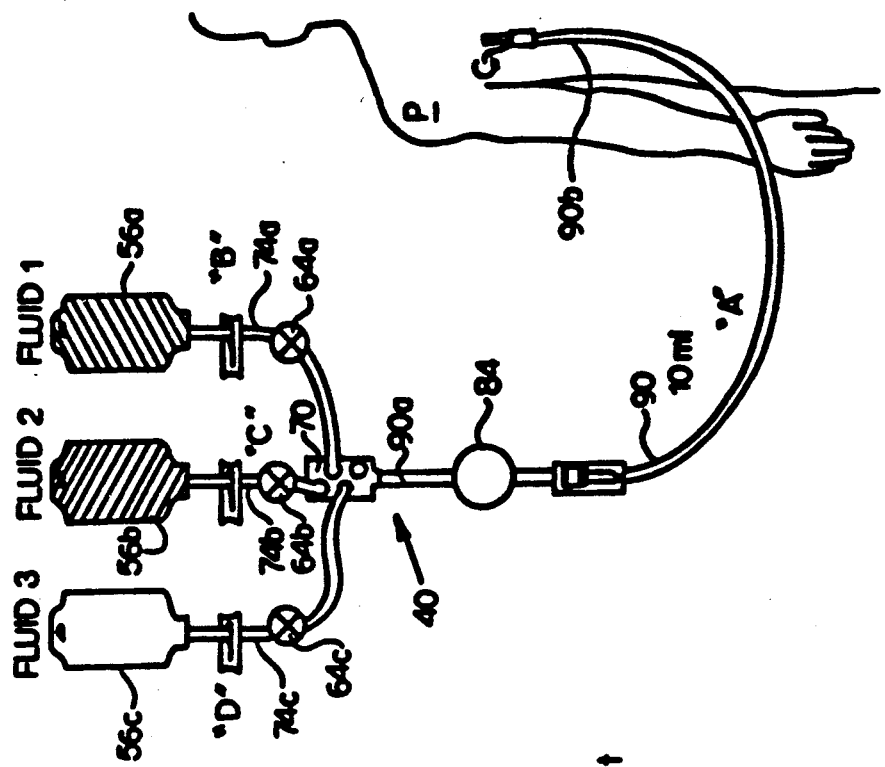
FIG. 11A is a schematic diagram of the system of FIG. 2 used to provide a three component fluid flow to a patient.

FIG. 11A illustrates schematically the system 40 coupled to a patient P where 3 containers 56a, 56b and 56c have been coupled to the fluid-flow junction member 70. In accordance with the parent application, the corresponding electrically actuated occluders 64a, 64b and 64c are sequentially opened and closed to permit fluid flow of pulses or quanta of corresponding fluids from the containers 56a, 56b and 56c through the conduit members 74a, 74b and 74c in a predetermined sequence. In this multiplexing mode, a fluid flow composed of a sequence of discrete pulses or quanta of fluids from the containers 56a, 56b and 56c is formed in the output tubing member 90.

The same order of fluids is to be delivered by the system of FIG. 11A as was previously to be delivered with the system 10 of FIG. 1A. That is, 20 ml/hour of fluid 1, 20 ml/hour of fluid 2 and 50 ml of fluid 3 at 100 ml/hour.

Figure 11B:
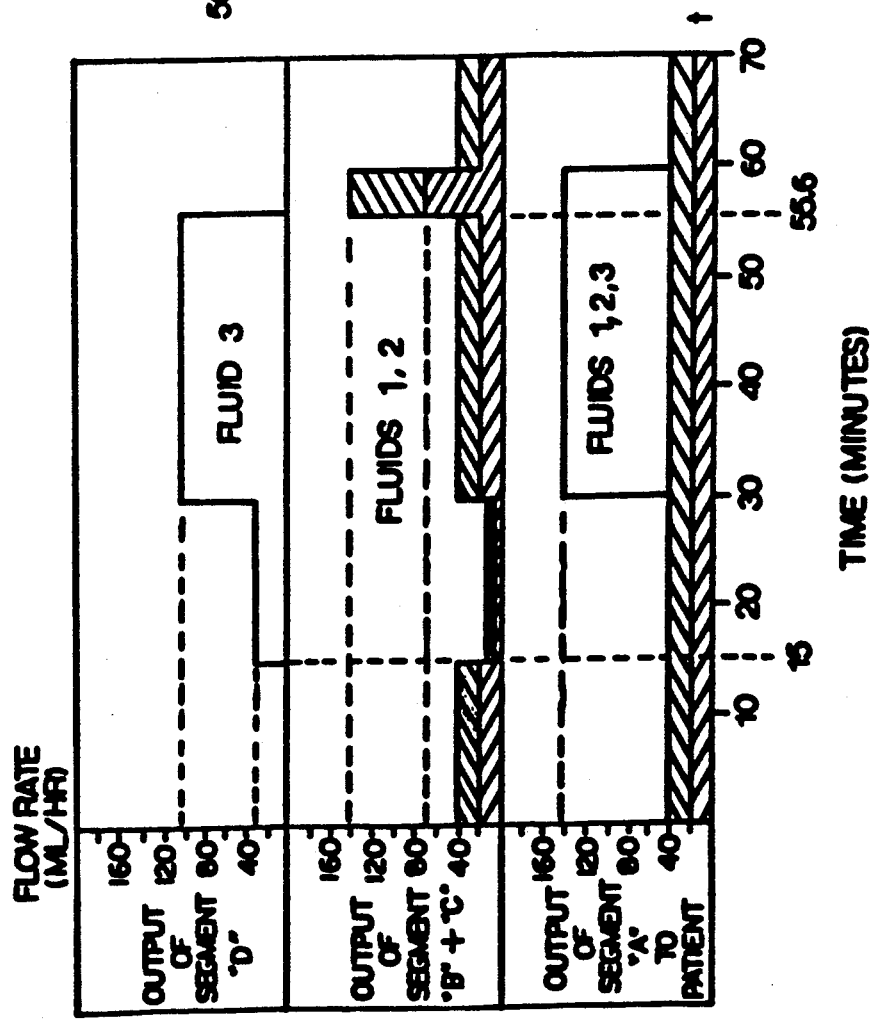
FIG. 11B is a set of graphs of fluid flow vs. time for the system of FIG. 2.

With reference to FIG. 11B, and in contradistinction to the graphs of FIG. 1B, fluid 3 from the container 56c, which is to be provided at a 100 ml rate to the patient for a 30 minute period, as illustrated at the top most graph of FIG. 11B is initially started at the 15 minute point with a flow rate of 30 ml per hour. Simultaneously, the flow rates for fluids from containers 56a and 56b have been substantially reduced from 20 ml per hour each to about 10 ml per hour. During the 15–30 minute time interval as illustrated in the bottom graph of FIG. 11B, fluid flow to the patient P continues unchanged at 20 ml per hour of each fluid.

At the 30 minute point, the flow rate for fluid 3 from the container 56c is increased by the system 40 to 100 ml per hour. This flow rate is maintained until the 55 minute point has been reached. Note that the order, as was the case with the order of FIGS. 1A and 1B calls for 100 ml of fluid 3 to be delivered to the patient P for 30 minutes.

As illustrated in the lower graph of FIG. 11B, output to the patient P from the line 90 corresponds to 100 ml of fluid 3 for 30 minutes. Notwithstanding the fact that fluid 3 flow from the container 56c has terminated at the 55 minute point, flow to the patient P of fluid 3 continues to the 60 minute point at the prescribed flow rate. Also, during the time period 55–60 minutes, this rate of flow of fluids 1 and 2 has been substantially increased to 70 ml per hour for each fluid as illustrated in the middle graph of FIG. 11B. However, output to the patient P of fluids 1 and 2 as a result of the multiplexing of the present system continues at a 20 ml per hour rate.

Thus the system 40 has delivered exactly the prescribed fluid combination, fluid 1 at 20 ml per hour, fluid 2 at 20 ml per hour and fluid 3 at 100 ml per hour for 30 minutes. In contradistinction, as illustrated in FIG. 1B the prior art stacking system of FIG. 1A delivered a substantially different fluid flow to the patient.

In connection with the multiplexing mode of operation, the detailed sequence for entry of the various drugs or solutions could be the same as the procedure discussed above for multiple drug delivery. The system 40 has the capability of automatically multiplexing drugs assigned to a pump if one or more of the drugs which has been assigned is to be infused continuously and one or more of the drugs is to be infused intermittently. In addition, a flush may be assigned to the pump that will be carrying out the multiplexing.

To check the status of the multiplexing operation, the operator can display Screen 12. On lines 8 and 9 of Screen 12 the drug dopamine in the solution dextrose are being infused through occluder 4 at a 30 ml per hour rate. In lines 11 and 12 of Screen 12 the drug Aminophylline in dextrose is being infused through occluder 5 at a 15 ml per hour rate. On lines 14 and 15 of Screen 12 the system 40 has indicated that the fluid Heparin is being infused to the patient through occluder 6 at a 25 ml per hour rate.

In those instances where an intermittent drug, such as fluid 3 of FIG. 11A has been scheduled during the multiplexing of continuous drugs, such as fluids 1 and 2 of FIG. 11A, the system 40 will automatically predict when the infusion of fluid 3 should be initiated or terminated such that the output to the patient corresponds to the ordered fluid flow sequence. With respect to FIG. 11B, if the 30 minute time period is a point at which the fluid 3 should be reaching the patient at a 100 ml per hour rate, prior to that time period the system 40 will determine an intermediate time period wherein the fluid 3 should be permitted to flow into the output tubing 90 which is coupled to the patient.

As a result of this prediction by the system 40, during the intermediate time period prior to the 30 minute period fluid 3 will begin flowing. However, there will be no delivery of fluid 3 to the patient until the 30 minute time period when the system 40 switches from its original schedule of equal quantities of only fluid 1 and fluid 2 to the required delivery schedule of equal flow rates of fluid 1 and 2 and a substantially greater fluid flow rate of fluid 3.

FIG. 11C is a graph illustrating the fluid aspects of the multiplexing of the system 40. The graph of FIG. 11C corresponds to the multiplexing operation with respect to the order to be delivered to the patient in the lower graph of 11B.

With respect to FIG. 11C, fluids 1 and 2 are initially each alternately permitted to flow into the fluid flow junction 70 by respective occluders for approximately 11 and ½ seconds. During this initial phase which corresponds to a time period of 0 to about 15 minutes there is a steady state condition established wherein an 11 and ½ second long pulse or bolus of fluid 1 is permitted to flow into junction 70. Immediately thereafter an 11 and ½ second long bolus or pulse of fluid 2 is permitted to flow into the fluid flow junction 70.

This process continuously repeats itself for first 15 minutes during the initial phase of operation of the system 40. During this time interval the spaced-apart pulses or quanta of fluid 1 which enter line 90 at an entry port 90a are spatially positioned between spaced-apart quanta or pulses of fluid 2. As the quanta of fluids 1 and 2 move through the tubing member 90, they are mixed together such that when they arrive at an output port 90b at the catheter C of the patient a uniform mixture is delivered to the patient 50% of which corresponds fluid number 1 and 50% of which corresponds to fluid number 2.

Prior to the 15 minute point, the system 40 has determined that it will be necessary to initiate flow of fluid 3 so as to minimize fluid transients to the patient and so as to deliver the ordered fluids at the required flow rates. During this compensation phase or interim phase which extends from about the 15 minute point to the 30 minute point at which the fluid 3 should be delivered to the patient at a rate of 100 ml per hour, the system 40 is sequentially actuating each of the occluders associated with containers 56a, 56b and 56c. The result of this actuation, as illustrated in FIG. 11C, is to continue to provide fluids 1 and 2 in 11.5 second quanta but after fluid 2 to inject a 57.5 second quantum of fluid 3, via occluder 54c, into the fluid flow junction 70.

This three fluid multiplexing operation is continuously repeated from the 15 minute time point to the 30 minute point. This results in a sequence of spatially spaced apart quanta of fluids 1, 2 and 3 moving into the conduit 90 at the input port 90a. By the time the sequence of quanta of fluid 1, sequence of quanta of fluid 2 and sequence of quanta of fluid 3 arrive at the output port 90b they will be mixed and provide a composite fluid flow output rate at a 140 ml per hour rate with fluid 1 being provided at a 20 ml per hour rate, fluid 2 being provided at a 20 ml per hour rate and fluid 3 being provided at a 100 ml per hour rate.

At the 30 minute point, the system 40 will again switch. At the 30 minute point, the fluid flow rate jumps to 140 ml per hour. At this time, fluid 1 is permitted to flow for a 3.3 second interval, fluid 2 is permitted to flow for a 3.3 second interval, and fluid 3 is permitted to flow for a 16.4 second interval This sequence is repeated for 25.6 minutes which corresponds to a time of 55.6 minutes.

Prior to the 55.6 minute point, the system 40 will have predicted that it will be necessary to terminate flow of fluid 3 from the container 56c. A second compensation phase will be needed. Hence, at that time occluder 64c will be deenergized and flow of fluid 3 from the container 56c ceases. However, flow of fluid from the containers 56a and 56b continues during the time interval between 55.6 minutes and 60 minutes at a rate of 140 ml/hour.

In this second compensation phase, fluid 1 is permitted by occluder 64a to flow for 3.3 second time intervals. Similarly, fluid 2 is permitted by occluder 64b to flow for 3.3 second time intervals. Hence, during this compensation phase alternating pulses of fluid 1 and fluid 2 are permitted to enter the fluid flow junction 70 and exit to the input port 90a of the conduit 90. As the spatially spaced apart quanta of fluid 1 which are interspersed between the spatially spaced apart quanta of fluid 2 move through the conduit 90 they are mixed and arrive as a stream of 50% fluid 1 and 50% fluid 2 at the output port 90b.

At the time equals 60 minute point, the fluid flow rate drops to 40 ml per hour and fluids 1 and 2 continue to be sequentially injected into the fluid flow junction 70 for 11.5 second long time intervals. This then results in an output fluid flow to the catheter C at a rate of 20 ml per hour for each fluid.

Figure 12:
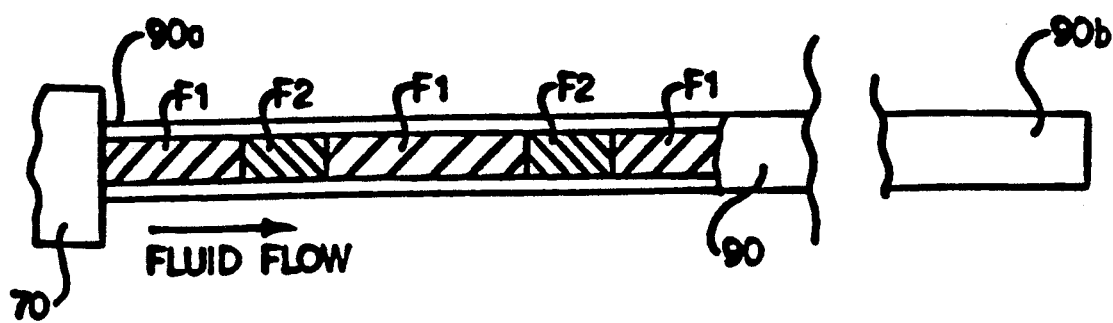

In further illustration of the multiplexing process, FIG. 12 is a schematic diagram of a plurality of spaced apart quanta of fluid one, each bearing an identification numeral F1. Interspersed between the quanta of fluid one is a spaced apart sequence of quanta of fluid two, each bearing an identification numeral F2.

The spaced-apart sequence of quanta of fluid one and the interspersed spaced apart sequence of quanta of fluid two enter the tubing member 90 at the input port 90a. The quanta are mixed while in the tubing member 90 and at the output port 90b is a fluid flow at a designated rate which includes fluids one and two in equal proportions.

It will be understood that the process of predicting when the system 40 should switch from a first predetermined flow sequence to an intermediate or compensating flow sequence and then to a second predetermined flow sequence is dependent on the volume of the tubing member 90. For purposes of the following discussion the tubing member 90 shall be assumed to be equal to 10 ml.

The present multiplexing system compensates for effective flow rate errors which occur when a solution's flow rate is changed. When operating in the multiplexing mode, the system 40 can simultaneously deliver a plurality of drugs and solutions with one infusion pump.

The effective flow rate of each drug at a given time is equal to the fraction of the drug in the tubing times the initial total (or pump) flow rate. For example, if the tubing 90 is filled with a mixture of ¼ drug A and ¾ drug B and the pump rate is 100 ml/hr, then the effective rate of drug A is 25 ml/hr and the effective rate of drug B is 75 ml/hr.

During steady state, the effective flow rate of each drug is the same as the desired rate. The rate errors occur when the pump rate is changed to a new rate, but the drugs in the tubing are mixed in proportion to the previous rates. This causes the effective flow rate of each drug to be in error until the tubing is flushed by the drugs running in the new proportion.

For example, assume that drug A is running at 20 ml/hr with drug B at 60 ml/hr. The total rate is 20+60=80 ml/hr. The tubing 90 contains 20/80=¼ A and 60/80=¾ B.

If the rate of A is changed to 40 ml/hr, the total flow rate is 40+60=100 ml/hr. The effective rates are now ¼*100=25 ml/hr for A, and ¾*100=75 ml/hr for B. The errors are 100*(25−40)/40=−37.5% for A, and 100*(75−60)/60=25% for B.

These effective flow rate errors will continue until the tubing 90 has been flushed. If the tubing volume is 10 ml, then flushing it will take 10 ml/100 ml/hr=0.1 hr=6 minutes. After the tubing is flushed, the effective rates will equal the desired rates.

In summary:

| | Effective flow rates (ml/hr): | | |
|---|---|---|---|
| | A | B | Total |
| Initial | 20 | 60 | 80 |
| Transition | 25 | 75 | 100 |
| Final | 40 | 60 | 100 |

| | Transition calculations: | |
|---|---|---|
| | A | B |
| Tubing mix | 20/80 = 0.25 | 60/80 = 0.75 |
| Effective rate | 0.25*100 = 25 ml/hr | 0.75*100 = 75 ml/hr |
| Rate error | $100 * \frac{(25-40)}{40} = -37.5$ | $100 * \frac{(75-60)}{60} = 25\%$ |

The system 40 automatically determines and inserts an intermediate or compensation phase between the Initial and the Final flow rates when carrying out the multiplexing function. This compensation phase is used to adjust the individual drug rates, in order to properly proportion the drugs in the tubing in preparation for the new flow rates.

The compensation phase is initiated ahead of the next scheduled flow rate change by the amount of time required to flush the tubing volume.

During the compensation phase, the individual drug proportions are adjusted to provide the desired mixture of drugs in the tubing at the start of the next scheduled flow rate change, with a total flow rate equal to the Initial flow rate. The result is that the output to the patient P is exactly as prescribed.

The following equation specifies the length of the compensation or intermediate phase D:

$$D = \frac{\text{VOLUME OF TUBING MEMBER 90}}{\text{PRESENT DELIVERY RATE}}$$

The time at which the compensation or intermediate phase should start corresponds to:

$$T = \text{TIME FOR SWITCHED OUTPUT TO OCCUR} - D.$$

Based on the length of the compensation or intermediate phase D, the system 40 can adjust the amount of time during which any given occluder is energized. By keeping the original fluid flow rate but adjusting the proportions of the constituent fluids the tubing member 90 can be flushed by the time that the prescribed fluid flow order requires a change to take place in the fluid flow to the patient.

The multiplexing process is a two step procedure. With respect to FIG. 13A, the system 40 carries out a continual volume generating process which keeps track of the amount of fluid to be delivered over a period of time in accordance with the rate previously entered by means of Screen 2. In an initial step 300, relative rates for each of the fluids to be delivered are established. In a step 302 accumulators are established for each of the fluids. The accumulators keep track of the quantity of fluid that should be delivered in accordance with the previously entered delivery schedule. In a step 304 a base time increment is determined. In a step 306 the system 40 waits for the duration of the based time increment. In a step 308 the contents of each of the accumulators is updated. The updated value of each accumulator corresponds to the amount of fluid that should have flowed for the base time increment at the relative rate.

Once each of the accumulators has been updated to reflect the total volume of the respective fluid which should have been delivered, the system 40 then returns to the step 306 and waits for the next time increment. The volume generating process continues updating accumulator values until new relative rates are provided.

Figure 13A:
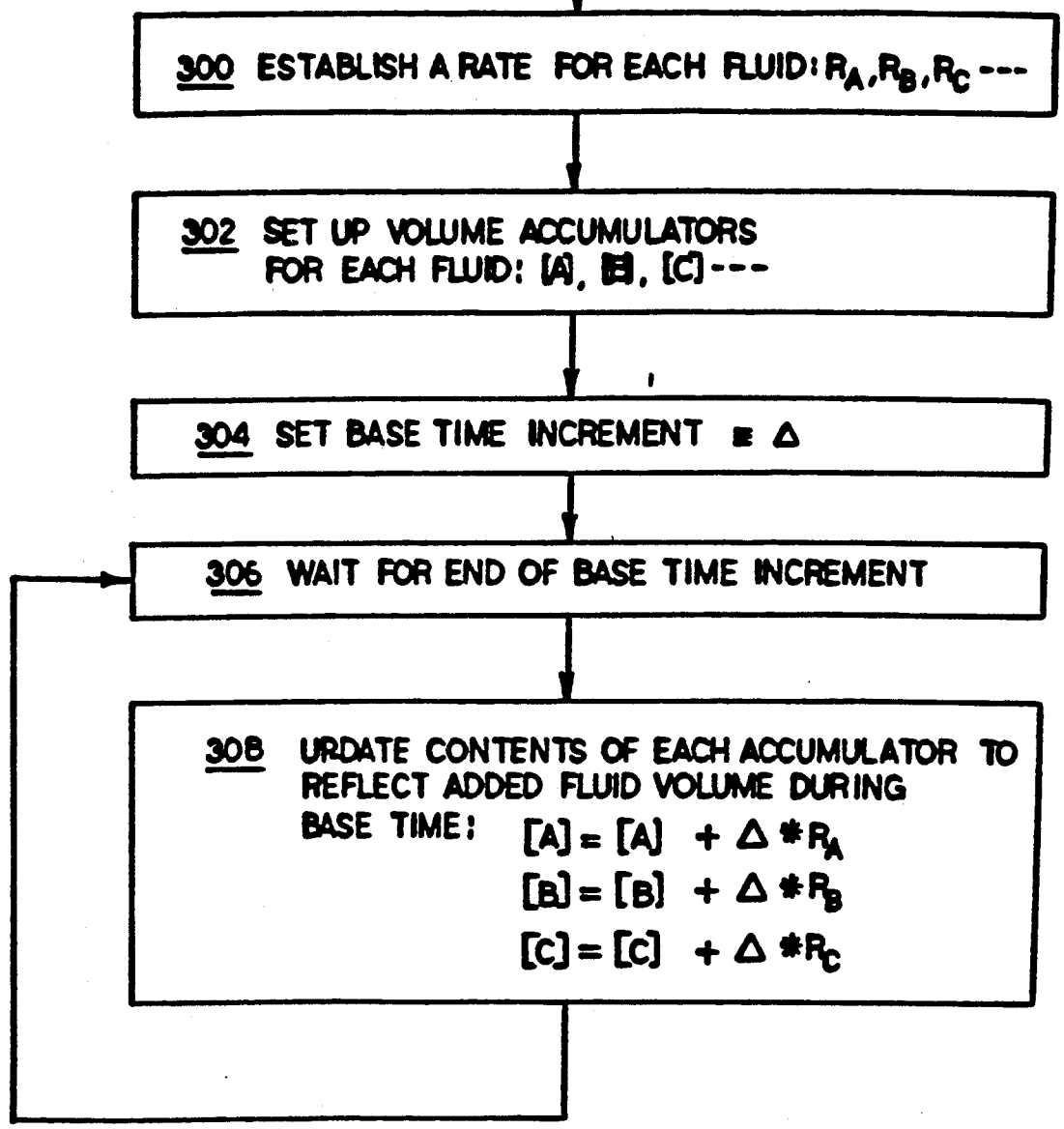
FIG. 13A and B together form a flow diagram of the method of multiplexing in accordance with the parent application.
Figure 13B:
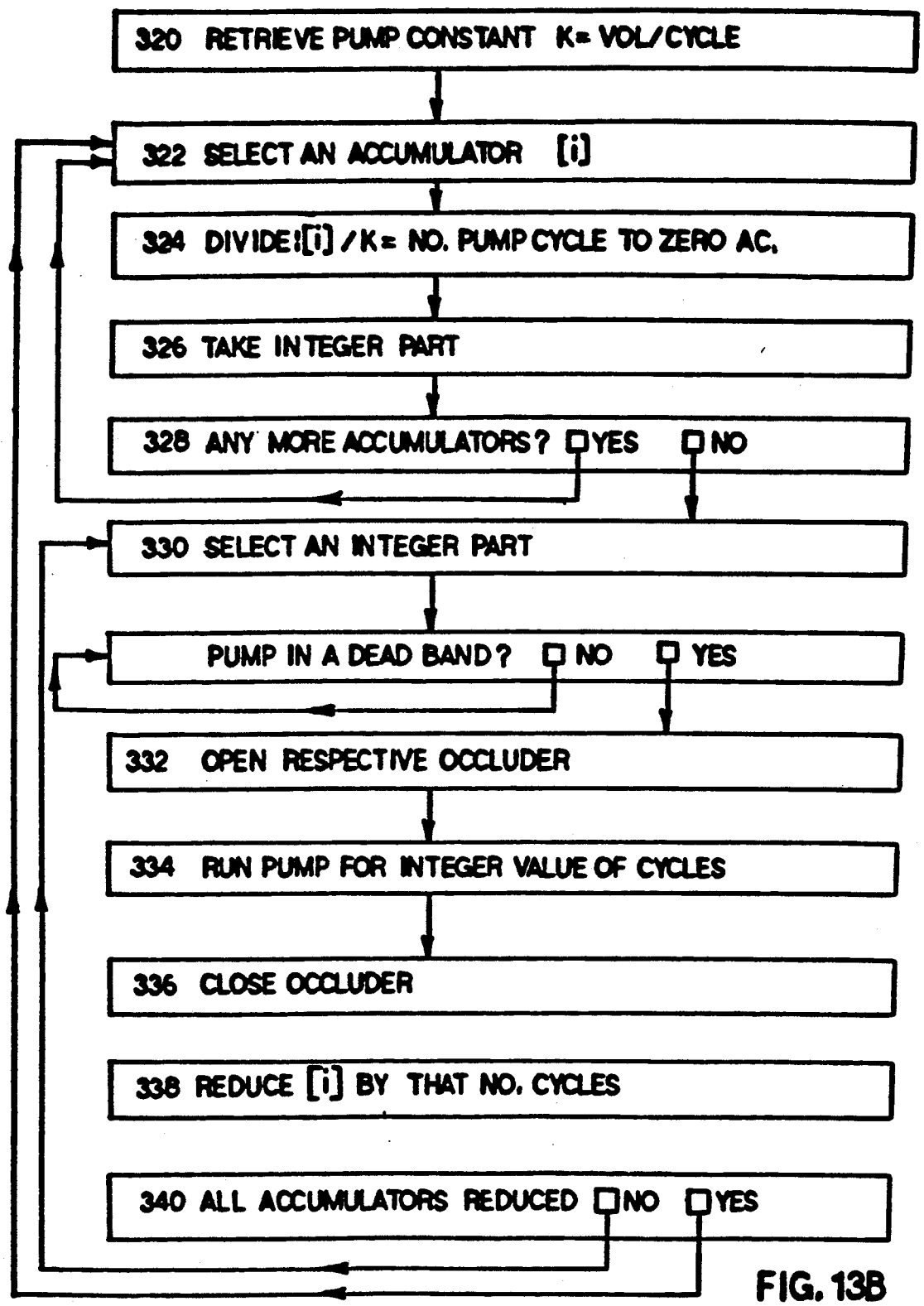

With respect to FIG. 13B the process of controlling the occluders assigned to the respective fluids to be delivered utilizes the continuously updated values in each of the accumulators. In a step 320 a pump constant corresponding to volume per revolution, or volume per linear movement in the case of a linear pump, is retrieved. In a step 322, one of the accumulators is selected. In a step 324 the contents of the selected accumulator is divided by the pump constant. This results in the number of pump revolutions needed to provide the quantity of fluid indicated by the contents of the accumulator. In a step 326 the system 40 takes the integer part of the number of pump revolutions. In a step 328 the system checks to see whether or not integer parts have been formed for all accumulators. If more are needed, the system returns to the step 322.

If integer parts have been formed for all of the accumulators the system 40, in a step 328, selects one of the integer parts. In a step 332 the system 40 opens a corresponding occluder. In a step 334 the system 40 runs the pump, such as the pump 84 for as many revolutions as corresponds to the selected integer value. In a step 336 the open occluder is then closed. In a step 338 the value in the corresponding accumulator is reduced by the amount of fluid just delivered in the step S34. In step 340 the system 40 checks to see whether or not all accumulators have been reduced. If not, it returns to the step 330 and selects another integer part associated with another accumulator. If so, the system 40 returns to the step 322 to select an accumulator and repeat the process.

In accordance with the above method, a sequence of pulses or quanta of each of the predetermined fluids is permitted to flow into the input in 90a of the output conduit 90 and is then pumped to the patient P by the pump 84. The above method produces the sequences of fluid quanta such as illustrated and previously discussed in FIG. 11C.

The occluder can preferably be opened and closed during the pump dead band interval. By so limiting the times when occluders can be opened or closed, only fluid quanta corresponding to integer numbers of pump "revolutions" will be delivered.

It will be understood that while a particular example of a drug or solution regime was discussed with respect to Screen 2, drugs or solutions may be specified to the system 40 in a variety of ways without departing from the spirit and scope of the parent invention. For example, a drug or solution program could be specified through the bar code reader portion of the light pen 98. Alternately the desired regime of drugs and/or solutions could be supplied to the system 40 via telecommunications through one of the RS232 ports or the modem 156. Finally, the system 40 could contain in its memory a data base of drug names and doses. The drug names and doses could be displayed on the display unit 96 in response to appropriate input by the operator via the light pen.

Further, it will be understood that patient information can be input to the system 40 via the display unit 96. Screen 13 illustrates a patient information input screen. By means of such a screen, an operator can enter information such as the patient's name on line 7 as well as physical information such as sex and age on line 9, height and weight on lines 12 and 14 and allergies on line 16.

The printer 99 can provide a variety of hard copy reports which are in the nature of historical summaries of patient condition and delivered fluids over various periods of time. For example, and without limitation, attached hereto in the Addendum as Report 1 is a Physician Summary Report which can be generated by the system 40 upon request. In addition to patient identification information, the report can include information formation concerning vital signs, drugs which have been administered as well as comparisons of drugs to various vital signs.

In addition to those applications discussed above, the system 40 can be used for a variety of different purposes. This includes, patient monitoring using invasive and noninvasive sensors. Vital signs, temperature, respiration rate, pressures, and urine output could be monitored collected information can be used to turn drug pumps on or off.

The system 40 could be part of a closed loop feedback system that could couple drug dosing algorithms with sensors to create a servo mechanism and maintain prestated physical requirements. Specific examples include vasoactive drugs for blood pressure control and antibiotic pharmacokinetic measurements for disease control.

The catheters that currently feed drugs into the patient's venalsystem could be scheduled also to draw blood on command into an automatic blood testing system at the bedside for routine tests such as insulin, blood gases, or electrolytes.

By incorporating a pH sensor with a fetal heart rate monitor, the system 40 could detect fetal stress and automatically alarm and signal reduction in pitocin or other contraction type drugs which are known to create acidosis.

In either automatic or manual modes, in addition to IV drugs, the system 40 can quickly report other drugs given, other supplies given, other foods given, nursing time at the bedside, and all other routine bedside record keeping support tasks necessary for reduced administrative and medical cost containment.

By using computer curve fitting to predict the rate that a powder, tablet or high concentration liquid drug will dissolve in standard diluents, the system 40 could automatically maintain a consistent level of drug dose to the patient. Current technology tries to find a drug carrier matrix that dissolves evenly; this would not be necessary with matching of the dissolution curve with the drugs involved.

In addition, by gathering drug data and coupling it with sensor data, physician trending and relationship graphs will provide insight to patient drug response and will assist in patient management. This data is available both locally in a patient's room and remotely at the physician's home or office for more responsive drug management.

Since the system 40 has characteristics which tend to reduce patient sepsis and to reduce patient blood contact to one central IV line, patients who have immunosuppressed conditions can more favorably be treated. These patients include patients receiving chemotherapy, those with AIDS, bone marrow transplant patients, and others.

The system 40 could also be used to assist in patient pain management. With the addition of a small pushbutton on a cord to the patient, analgesia type drugs can be dispensed in predesignated quantity by patient demand. When the patient is alert enough, this is a proven method to reduce total morphine levels while better serving patient needs. Current systems are expensive and bulky. They use special standalone pumps with high cost narcotic drug containers. The system 40 could greatly simplify this technique while significantly reducing cost.

Figure 14A:
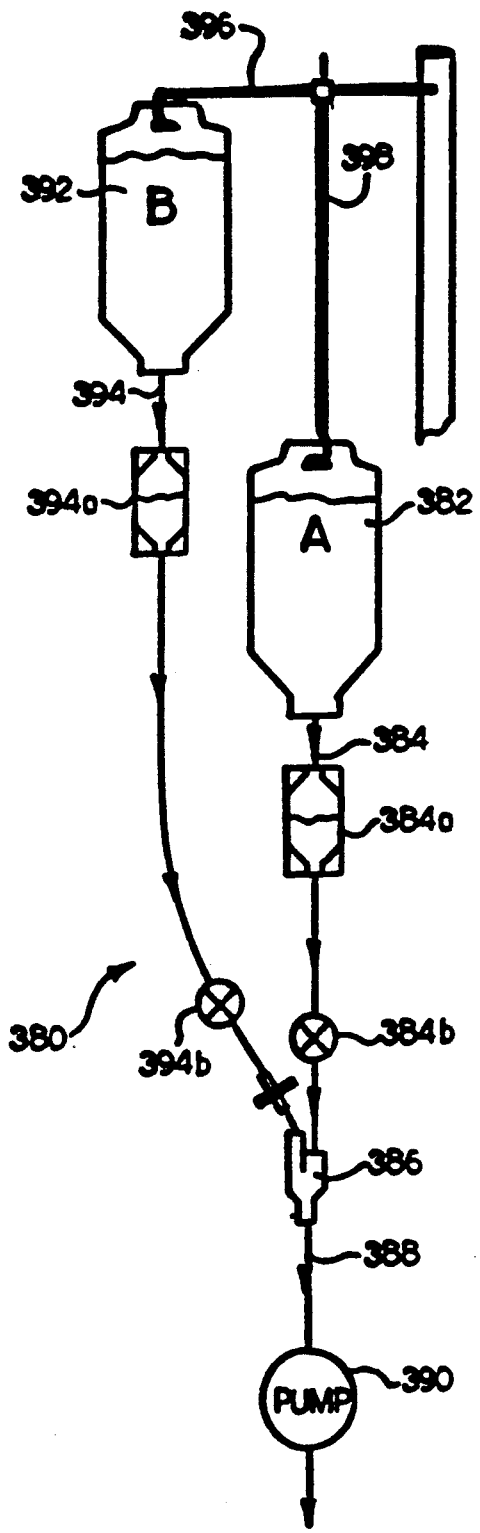
FIG. 14A illustrates a prior art apparatus for introducing a second fluid into a flow of a first fluid.

The improved operational characteristics of the system 40 are readily apparent when compared to a known apparatus 380, FIG. 14A, for the purpose of introducing a second fluid, fluid B, into a flow of a first fluid, fluid A. The system 380 includes a solution container 382 which serves as a source of the fluid A.

Flow of the fluid A from the container 382 is carried by a conventional tubing member 384 which can include a drip chamber 384a. The tubing member 384 can be clamped shut by a manually operable clamp 384b. The tubing member 384 terminates at a Y-junction 386. Outflow from the Y-junction 386, via a tubing member 388, passes through a conventional infusion pump 390 and is then delivered to the patient at a rate determined by the setting of pump 390.

Fluid B, in a container 392 flows therefrom via a tubing member 394, through a drip chamber 394a and is regulated by a manually operable clamp or occluder 394b. Outflow from the tubing member 394 is coupled through the Y-junction 386 and can then flow into the tubing member 388.

The two fluid system of FIG. 14A has been commonly used in situations where fluid A is being delivered to a patient and it is desirable to interrupt the delivery of fluid A for the purpose of delivering fluid B. Usually the volume of the fluid B in the container 392 is less than the volume of the fluid A in the container 382.

To provide an additional head to the fluid B, it is supported on a hanger 396 above the container 382. The container 382 is conventionally lowered by means of a short metal hanger 398. When the flow of fluid B from the container 392 is initiated, due to a difference in heights of the two containers 382 and 392, the fluid B will drain through the tubing member 388 and in the process will interrupt the flow of the fluid A through the tubing member 388.

Figure 14B:
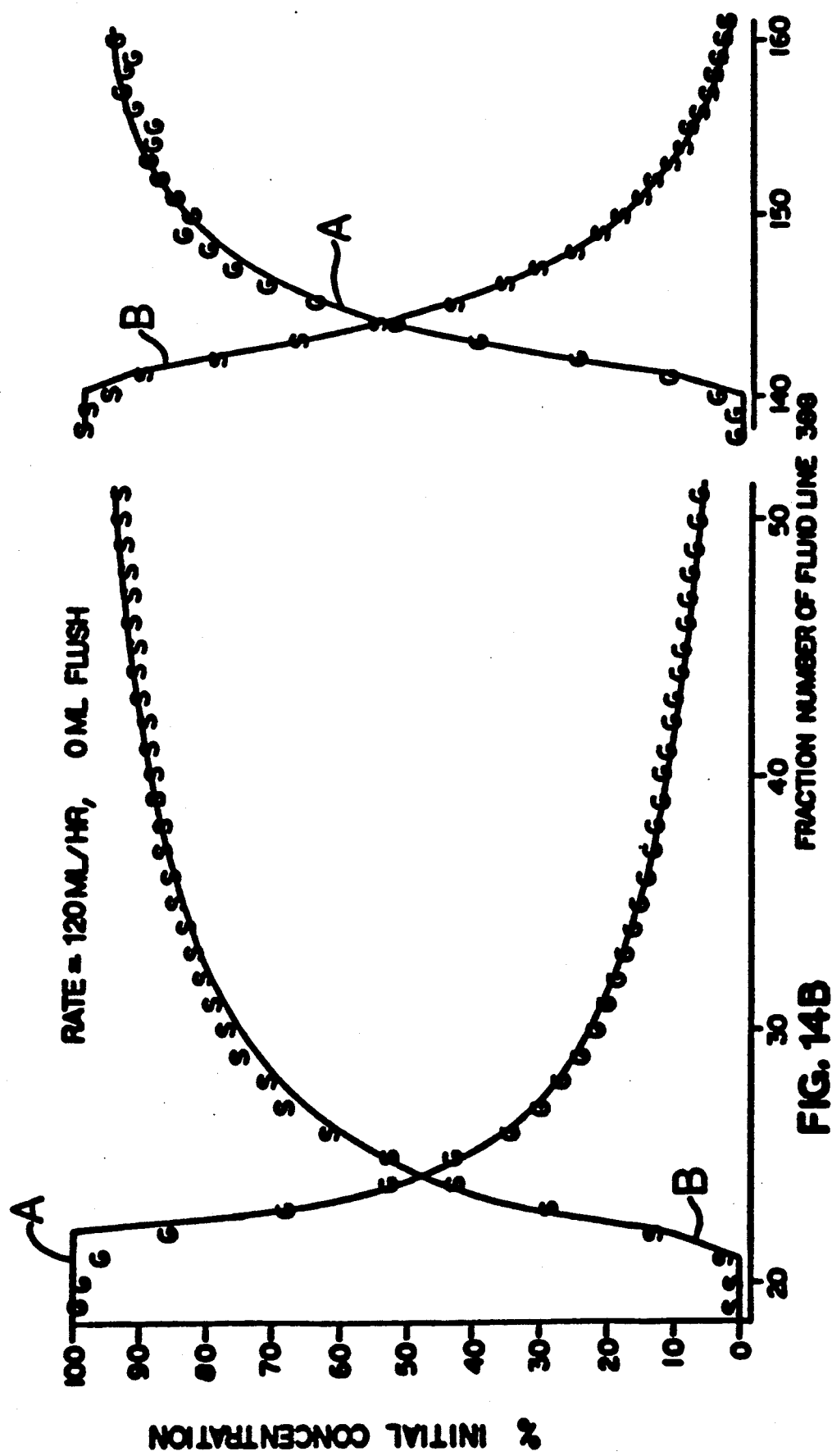

FIG. 14B is a pair of graphs illustrating the change in concentration of fluids A and B in the tubing member 388 as fluid B drains therethrough. As illustrated in FIG. 14B, initially fluid A corresponds to 100% of the fluid in the tubing member 388. As the fluid B starts to flow, the concentration of fluid A drops and the concentration of fluid B increases toward 100%. Subsequently, when the container 392 has been emptied the concentration of fluid B in the line 388 begins to decrease toward zero and the concentration of fluid A in the line 388 returns to 100%.

In FIG. 14B the "G" and the "S" identify measured data points. Each fraction corresponds to 0.4 ml.

In FIG. 14B, percent concentrations, as fluid A is displaced by fluid B and fluid B is displaced by fluid A, are plotted against fraction numbers of fluid in the line 388. The fluid delivery rate in the line 388 is 120 ml/hour. The fluid A could be for example, glucose and the fluid B could be saline.

FIG. 16 illustrates the calculated mixing volume for the system of FIG. 14A during the time intervals when fluids A and B are mixed in the line 388. During the initial mixing phase, the concentration of fluid B is increasing. During the final mixing phase, the concentration of fluid A is increasing. Total calculated mixing volume corresponds to 20.2 ml.

Fluid initial mixing volume was calculated starting from when fluid B first appeared and ending when fluid A fell below 5% of its initial concentration. Fluid final mixing volume was calculated similarly.

Figure 15A:
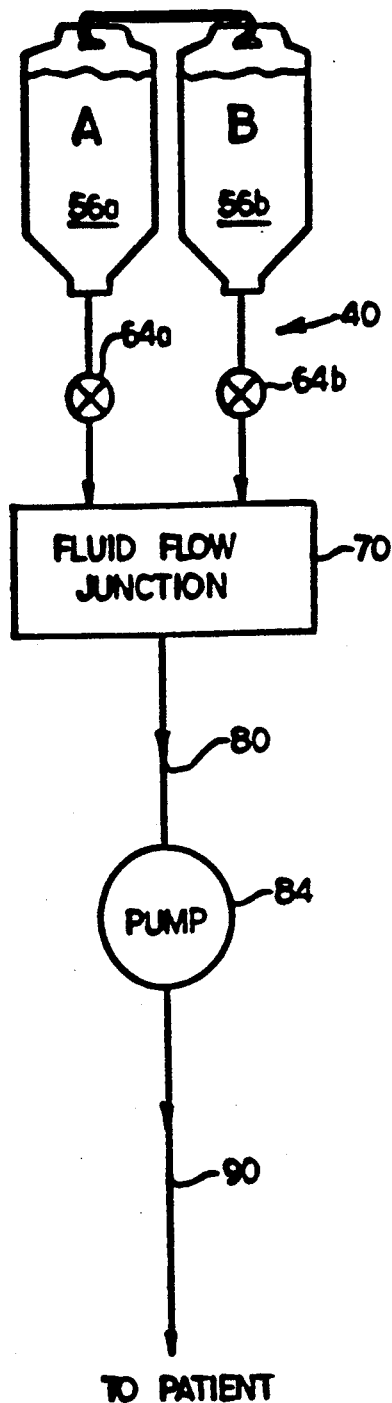
FIG. 15A illustrates a system for mixing fluids which employs computer controlled occluders.
Figure 15B:
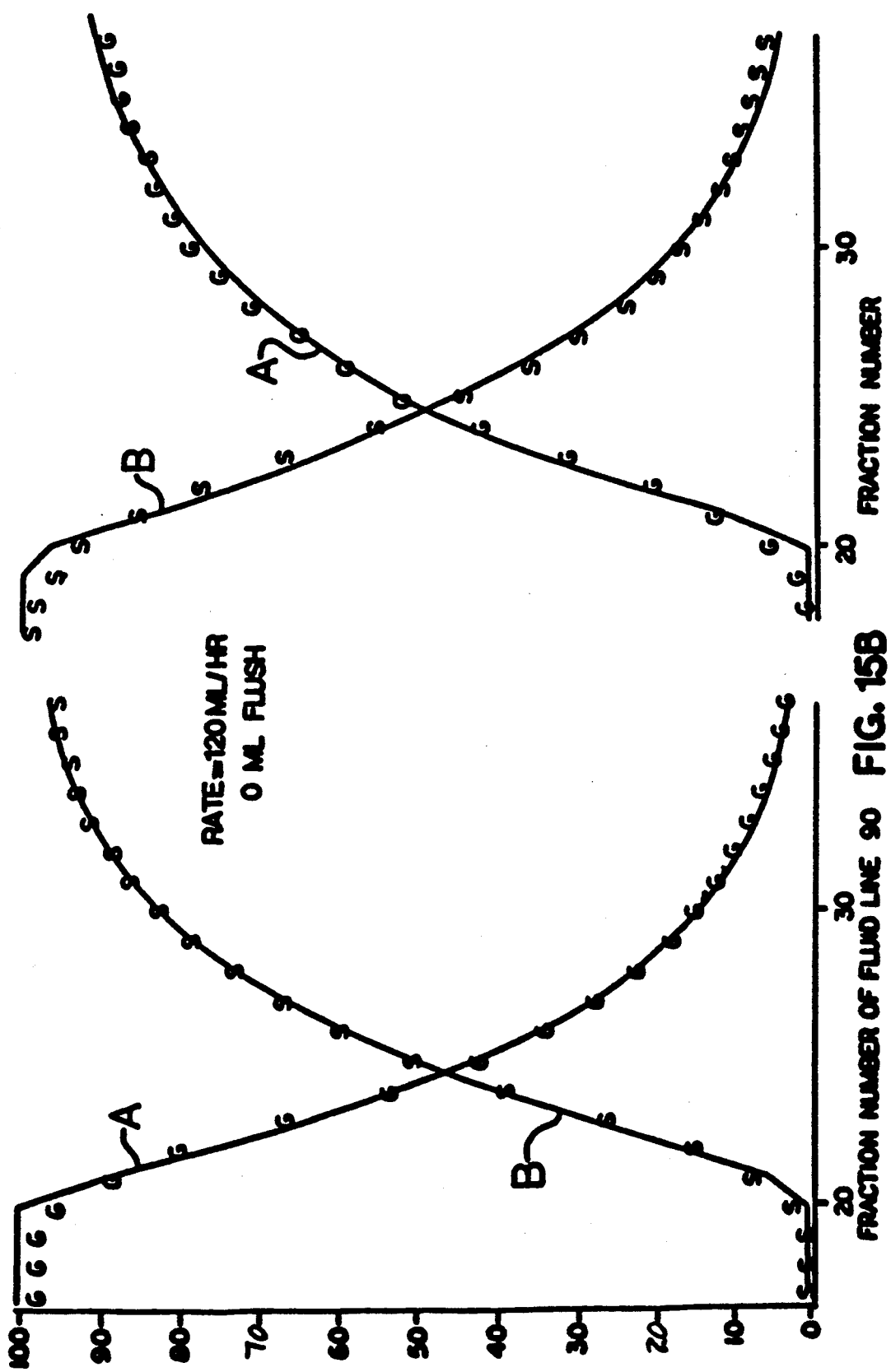
FIG. 15B is a pair of graphs illustrating the change in concentration of fluids A and B in the tubing member 90 of FIG. 15A.

In a similar study the system 40, see Figure 15A, utilized with two containers 56a and 56b containing fluids A and B and operated so as to deliver 120 ml per hour provides substantially different results. In FIG. 15B percent concentrations of fluid in the line 90 as the flow of fluid A is interrupted and switched to the flow of fluid B using computer controlled occluders 64a and 64b are plotted against the fraction number of fluid in the line 90. As is readily apparent from the graph of FIG. 15B, the flow concentration of fluid B in the line 90 increases substantially faster in the system 40 than does the concentration of fluid B in the line 388 of the system 380. As a result, the patient starts receiving the fluid B faster when administered by the system 40 than in the conventional prior art system.

Further, as illustrated in FIG. 16, the volume of the mixed fluids A and B during the transition intervals when fluid A is decreasing in the line 90 and fluid B is increasing as well as the reverse when fluid B is decreasing and fluid A is increasing has been calculated to be on the order of 11.9 ml. This latter value is about one-half the earlier noted value of mixing volume for the system 380. Hence, the volume of mixed fluids A and B is substantially less with the system 40. As a result, the possibility of interaction between the two fluids has been reduced. In addition, better control has been achieved over the delivery of the fluids to the patient.

Figure 17:
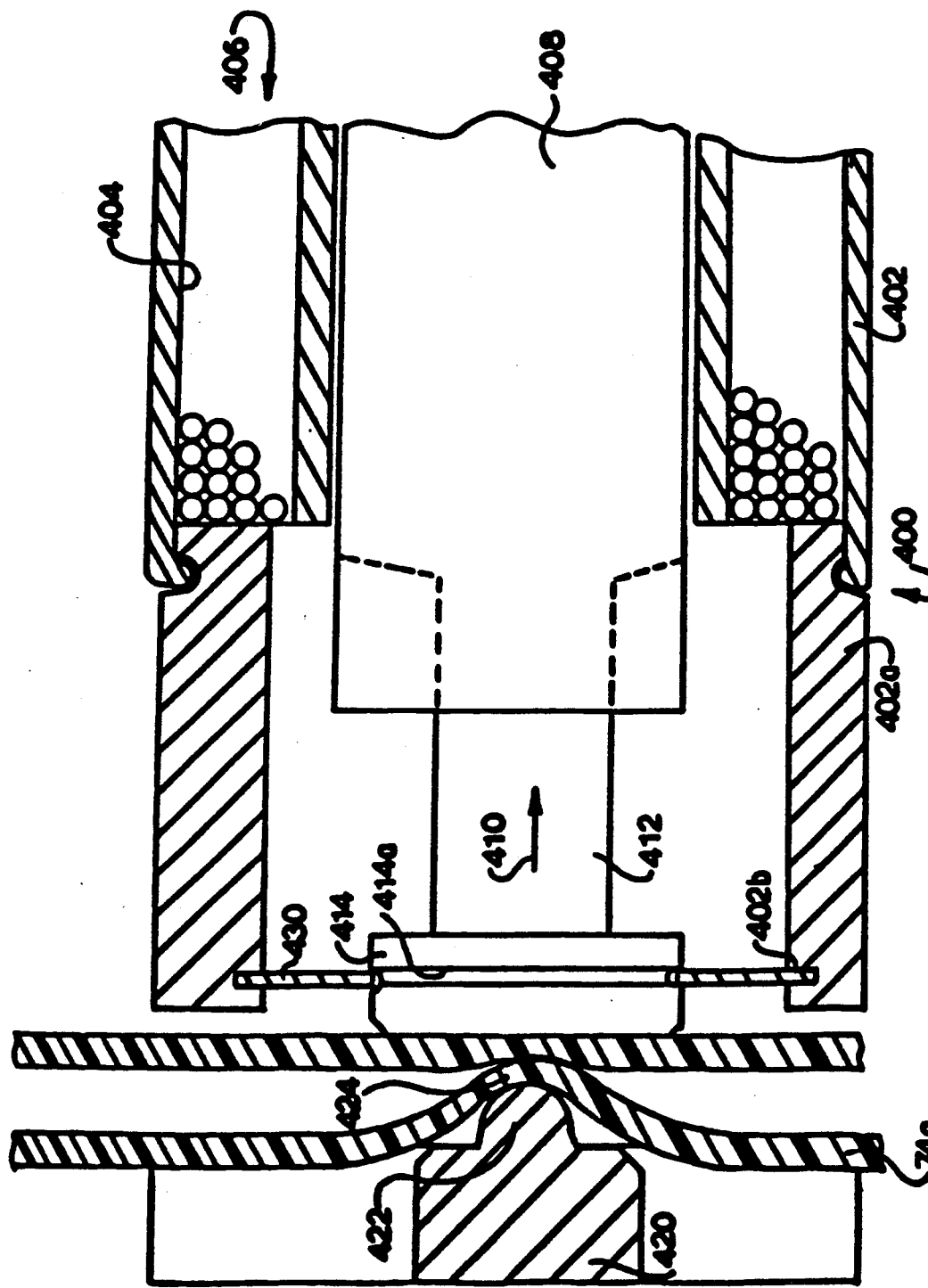

FIG. 17 illustrates an alternate occluder head 400 usable with the computer controlled occluders 64. The occluder head 400 includes a cylindrical solenoid body portion 402 defining an interior region 404 which is in part occupied by a solenoid coil 406. An extension 402a is crimped onto body portion 402.

Centrally located and axially movable within the housing 402 is a solenoid armature 408. The armature 408 is movable in a direction 410 in response to electrical energy having been applied to the solenoid coil 406. A compression spring, comparable to the spring 178 can be used to move the armature 408 opposite the direction 410 when the solenoid coil 406 is deenergized.

The armature 408 carries a cylindrical spacing member 412 which terminates in a disk-shaped head 414. The head 414, when the solenoid coil 406 is deenergized will pinch closed the tubing member 74a.

The occluder head 400 also carries a fixedly located clamping member 420. The member 420 terminates adjacent the tubing member 74a in a curved extension 422. As the solenoid armature 408 moves opposite the direction 410, the disk-shaped clamping member 414 forces a region 424 of the tubing member 74a against the curved member 422 which clamps the tubing member 74a shut. When the coil 406 is energized, the armature 408 and the disk-shaped member 414 move in the direction 410 away from the region 424 thus permitting a flow of fluid through the tubing member 74a.

An annular seal 430 located between a groove 402b in the housing extension 402a and an annular groove 414a in the disk-shaped member 414 seals the occluder head from incident spilled fluids as well as from cleaning fluids which might be used for the purpose of cleaning the exterior surfaces of the system 40. The annular seal of 430 could be formed of any flexible material which will be resistant to fluids and cleaning solutions of a type normally found in a healthcare environment.

It should be noted that while the previous discussions refer to the entry of information through the display 96 by means of the light pen portion of the bar code reader light pen member 98 it will be understood that such information can also be entered directly off of labels or documents by means of the bar code reading portion of that member in random order. For example, it would be possible to encode admission forms or other documents with a bar code which carries an indicium in each field in bar code format which specifies where on the corresponding screen the related information is to be entered. Additionally, by means of selected bar code characters it would be possible to invoke various functions through the bar code reader analogously to the way in which those functions are invoked by means of the light pen.

Hence, by means of the bar code reading portion of the member 98 preprinted data in a bar code format can be conveniently and quickly entered into the system 40. In addition, labels on the solution containers 56 can also be printed with bar code format encoded information identifying the related solutions, drugs, delivery rates and volumes. Such information can all be entered into the system 40 by means of the bar code reading portion of the member 98.

It will also be understood that a variety of other sensors can be coupled to the system 40 for the purpose of sensing and recording other patient related data. These sensors could include but are not limited to blood pressure sensors, temperature sensors or the like.

It will also be understood that the system 40 can be operated in a variety of ways. In one mode of operation, a flush fluid, such as saline, can be used to separate two otherwise incompatible fluids. Imposing a requirement that there by a quantum of flush fluid between spaced apart quanta of incompatible fluids can be carried out through the display monitor 96.

As an alternate to the use of a liquid as a flush fluid, a gas, such as air, or oxygen could be used as a flush. In such an instance, the gaseous flush quantum which is located between two spaced apart quanta of incompatible fluids is withdrawn from the patient delivery tubing member 90 immediately prior to coupling to the catheter C at the end 90c. Further, it will also be understood that when a gas is used as a flush fluid to space apart incompatible quanta of liquids, it is also possible to precisely measure the length of each liquid quantum and accumulate the number of quanta which are delivered to the patient to provide very precise volume and rate information.

As yet another alternate, air pressure can be used as an alternate to the pump 84 to drive the delivery of fluid in the line 90 to the patient. In this embodiment, the driving gas is injected into the tubing member 90, perhaps also functioning as a flush fluid, and forcing the fluid therein to the patient.

As yet another alternate, it will be understood that the system 40 could be used in a gravity flow mode without a pump. This results in a low pressure injection of fluid into the patient.

It will be understood that by means of optics, that it is possible to accurately determine the internal tubing diameter to control the volume of delivered fluid more precisely. This is particularly advantageous wherein the tubing member 90, which can have a nominal diameter on the order of 0.065 inches is a disposable which is regularly replaced. The replacement tubing may have an actual diameter which varies somewhat from the nominal value of the diameter. By use of this self-calibrating feature such diameter variations can be compensated for.

It will also be understood that in yet another embodiment, it is possible to differentiate between a quantum of liquid and a quantum of a gas such as air. This detection process utilizes the property that the transmissive or reflected characteristics of a liquid are different from those of a gas. Hence, it is possible to differentiate and determine the presence or absence of a liquid or a gas. As a correlation, such a device can also be used as an air detector for the purpose of eliminating undesirable air in the line 90.

Figure 18:
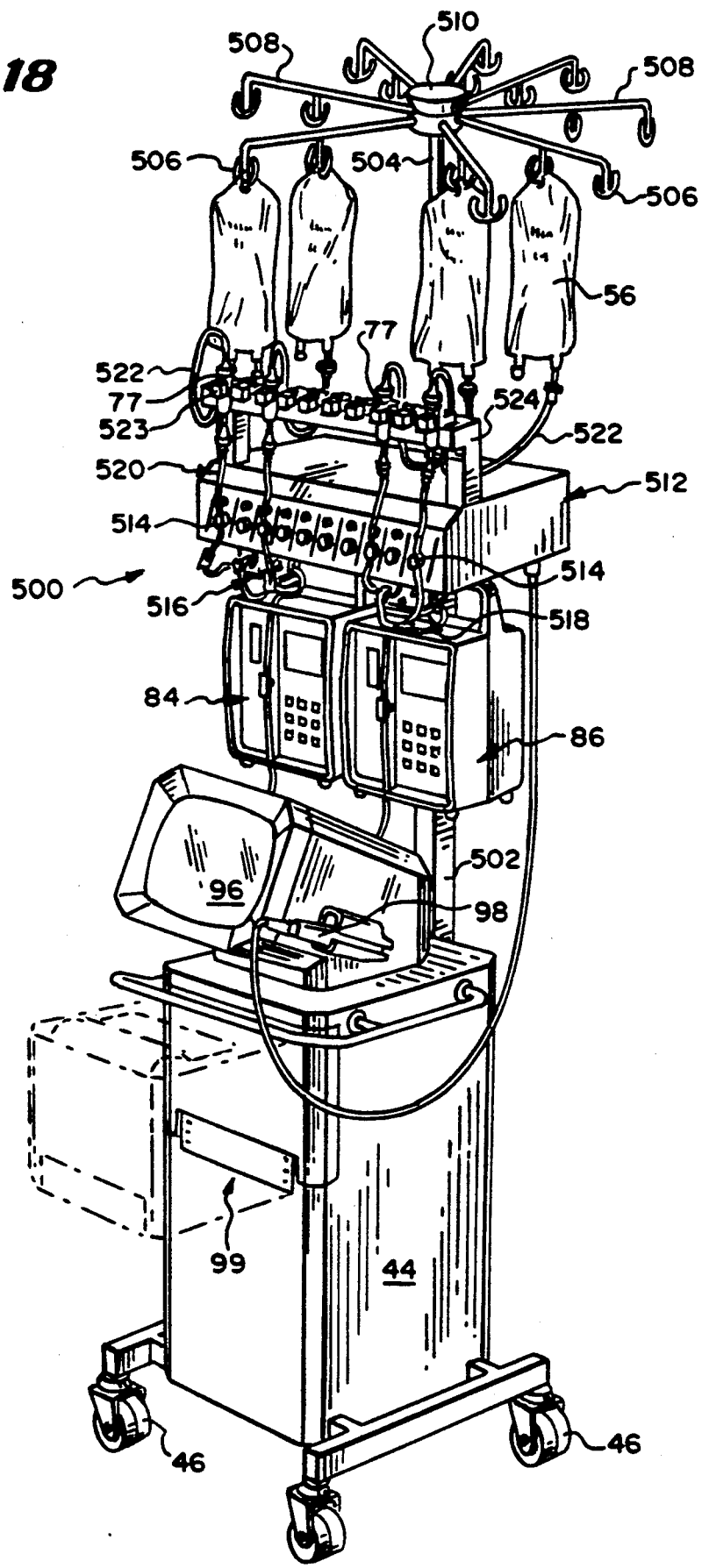

Referring now to FIGS. 18-27, the embodiments of the multi-fluid delivery system of the present invention are illustrated. Referring first to FIG. 18, an improved sealed multiple flow delivery system of the present invention is designated generally by the reference numeral 500. The multi-fluid delivery system 500 is functionally substantially the same as the multi-fluid delivery system 40 and accordingly the same numerals will be utilized where the same or functionally equivalent parts are described.

The system 500 includes a mobile base unit or housing 44 mounted on a plurality of casters 46. The housing 44 includes an upstanding standard or pole 502, which includes an upper end 504 onto which a plurality of hangers 506 are mounted by rods 508. The hangers 506 preferably are double hooked, such that a set of solution containers 56 can be hung from one hook, as illustrated. A second or replacement solution container (not illustrated) then can be hung from the second hook. The upper end 504 of the standard 502 also preferably includes an alarm light 510, which flashes to warn the operator of an alarm, which alarm preferably also is an audio alarm.

Also mounted on the standard 502, below the solution containers 56, is an occluder module 512, which includes an array of a plurality of independently actuable clamps or tubing occluders 514. The occluders 514 are functionally equivalent to the occluders 64, but include an improved tubing retaining structure as described with respect to FIGS. 19, 20 and 26. Located below the occluders 514 and mounted onto the module 512 are a first and a second fluid junction member 516 and 518, functionally equivalent to the fluid junction members 70 and 72.

Linking the solution containers 56 to the fluid junction member 516 and 518 through the occluders 514 are a plurality of fluid flow conduit members or tubing sets 520, preferably formed of transparent, flexible medical grade plastic tubing. The tubing sets 520 are functionally the same as the tubing sets 74 and include a drip chamber 77, which, however, is not mounted to the bag or container 56 as in the system 40, but instead is mounted separately from the container 56 by a tubing segment 522.

The tubing segment 522 provides the flexibility for the tubing sets 520 so that the drip chamber 77 can be mounted in a drip chamber array on a standard or holder 524 mounted on the module 512. The drip chamber 77 can be a conventional drip chamber system, which are automatically monitored in a conventional manner, such as by drop detectors 523. The system 500 can be set to alarm for various monitored conditions, such as fluid flow/no flow, fluid rate too slow/too fast, etc. The free hanging of the containers 56 and hence the drip chamber 77 of the system 40 (see FIGS. 2 and 4) can lead to errors due to movement or swinging of the container 56 and the drip chamber 77.

A further advantage of the fixed fluid array of drip chambers 77 is that the system 500 can automatically detect when the container 56 is empty utilizing the drop detectors 523. The amount of drugs in the containers 56 is very accurate, however, the total amount of fluid in the containers 56 can vary. The operator in the system 40 would have to visually watch the end of the fluid flow from a container 56 to ensure that the container is empty, since no automatic monitoring was provided.

The tubing set 520 is coupled through the pumps 84 and 86 which are mounted on the structure of the standard 502. The system 500 includes a video display 96, which can be utilized to display information and to input information utilizing the light pen of a light pen and bar code reader 98. The system 500 also includes a hard copy printer 99. The hard copy printer 99 provides a hard copy printout when desired and also functions as a last resort safety device.

The hard copy printer 99 includes an extra printer buffer, which is refreshed periodically and includes what drugs have been delivered and the schedule of what drugs are to be delivered. The information is always retained in the extra printer buffer, with only new data replacing old data upon refreshing. Upon a malfunction of the system 500, the information in the extra printer buffer is printed out, preferably automatically, on the printer 99 so that the current delivery information of the drugs is not lost. This provides a last resort safety feature for the system 500.

Figure 19:
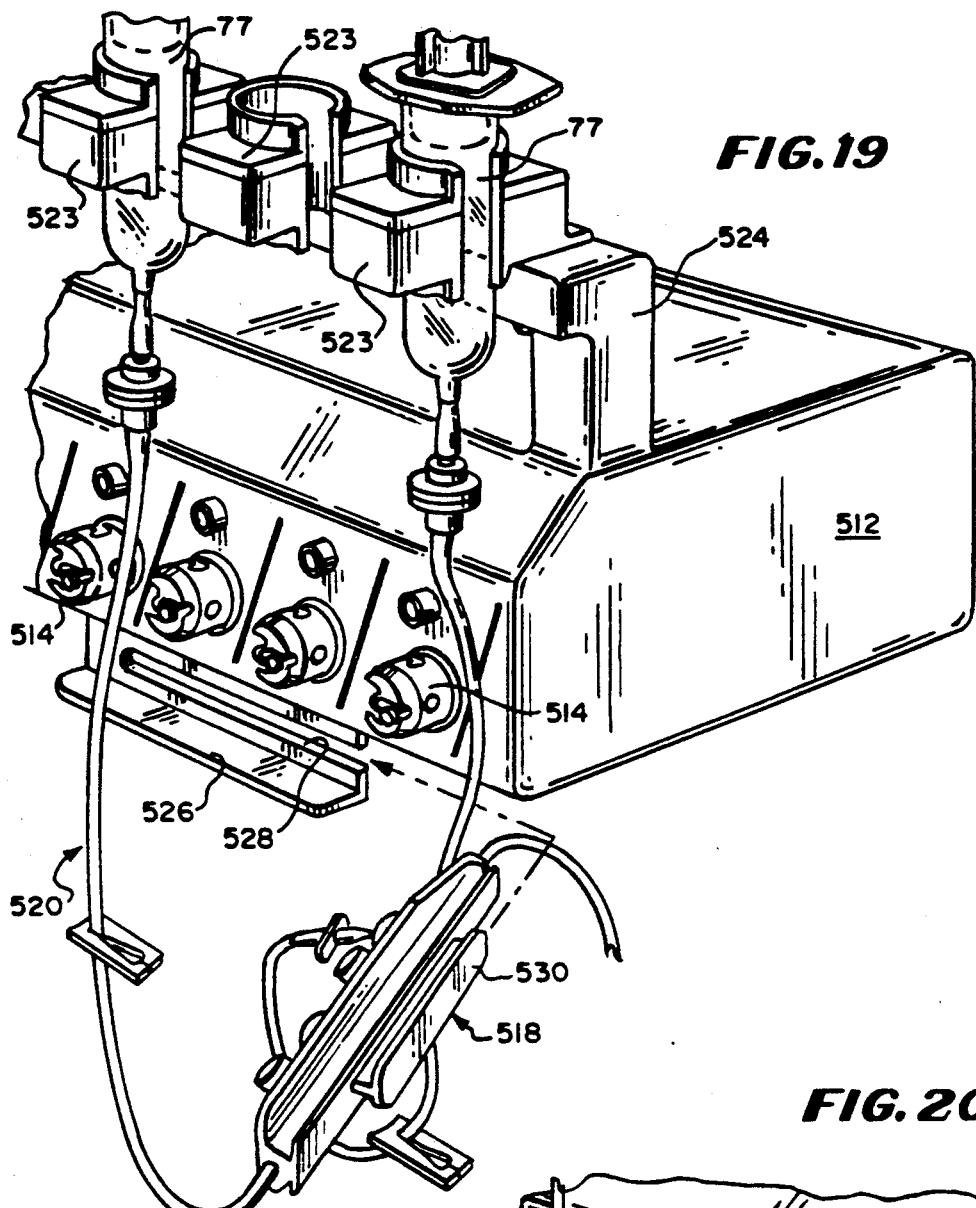
Figure 20:
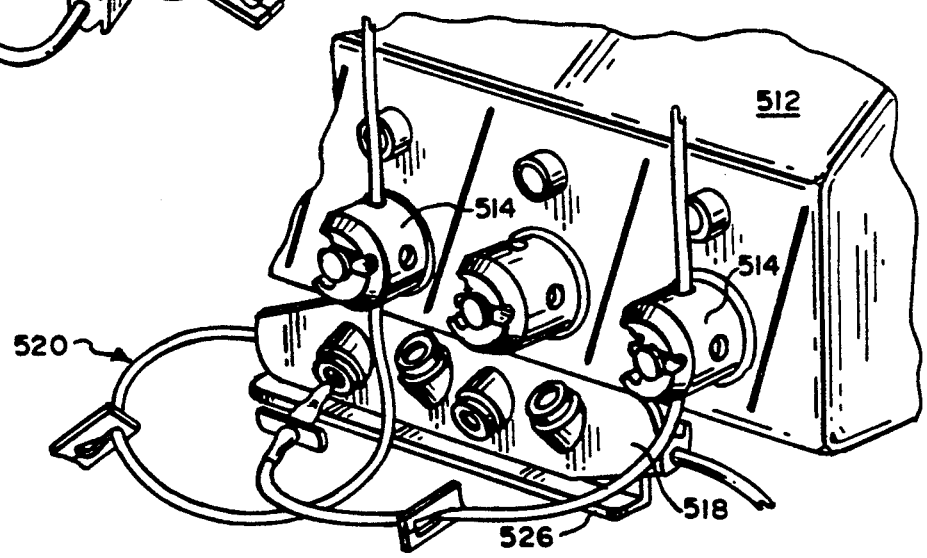

Referring to FIGS. 19 and 20, the occluder module 512 and mounting of the fluid junction member 518 and tubing set 520 thereto is best illustrated. The occluder module 512 includes a fluid junction member mounting bracket 526 having a slot 528 opening to one side therein. The fluid junction member 518 includes a base mounting flange 530, sized to fit securely into the slot 528 to secure the fluid junction member 518 to the occluder module 512. The drip chambers 77 and drop detectors 523 are mounted on the standard 524 and the tubing set 520 is secured in the occluder 514 (FIG. 20), as will be described with respect to FIGS. 26 and 27.

Figure 21:
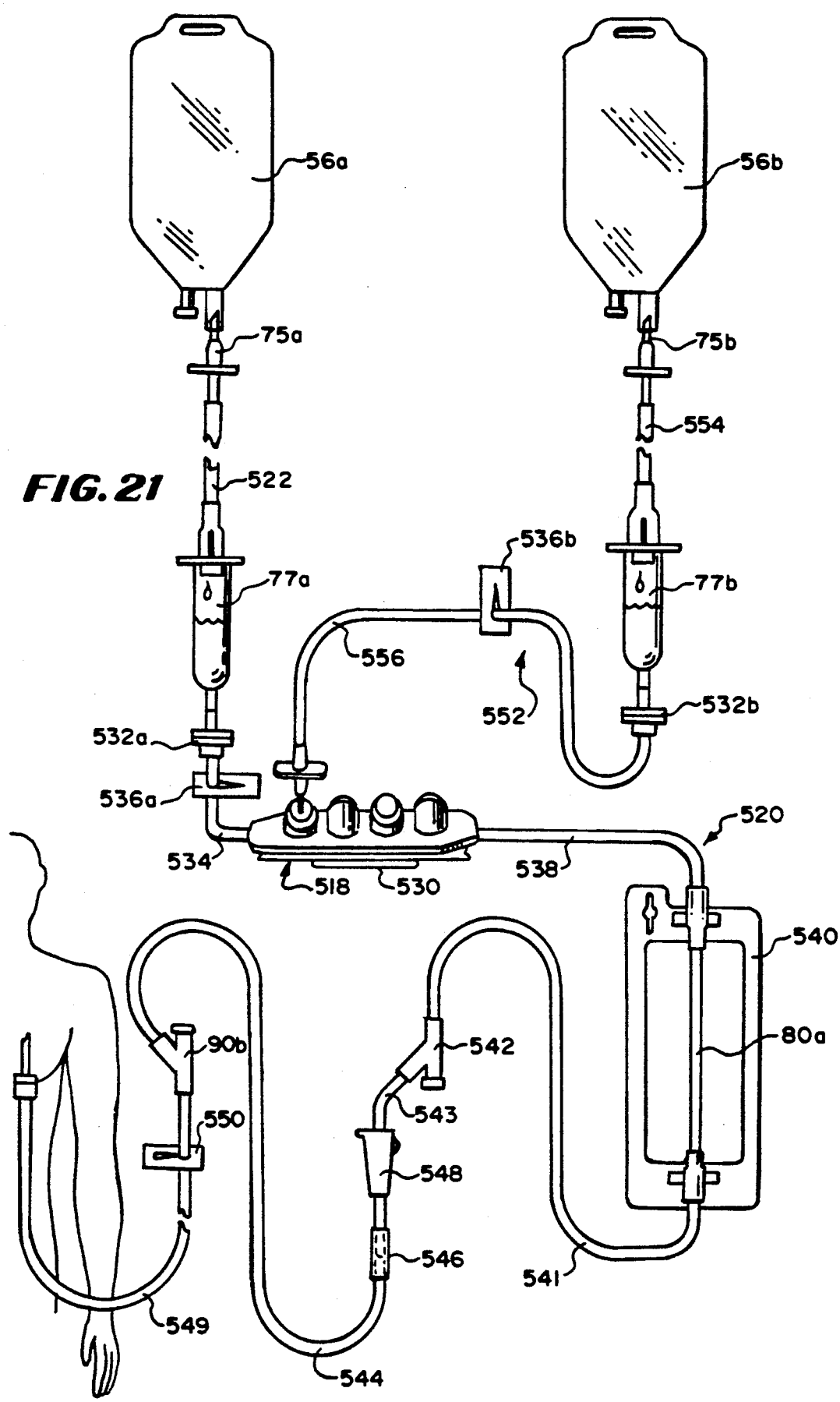
Figure 25:
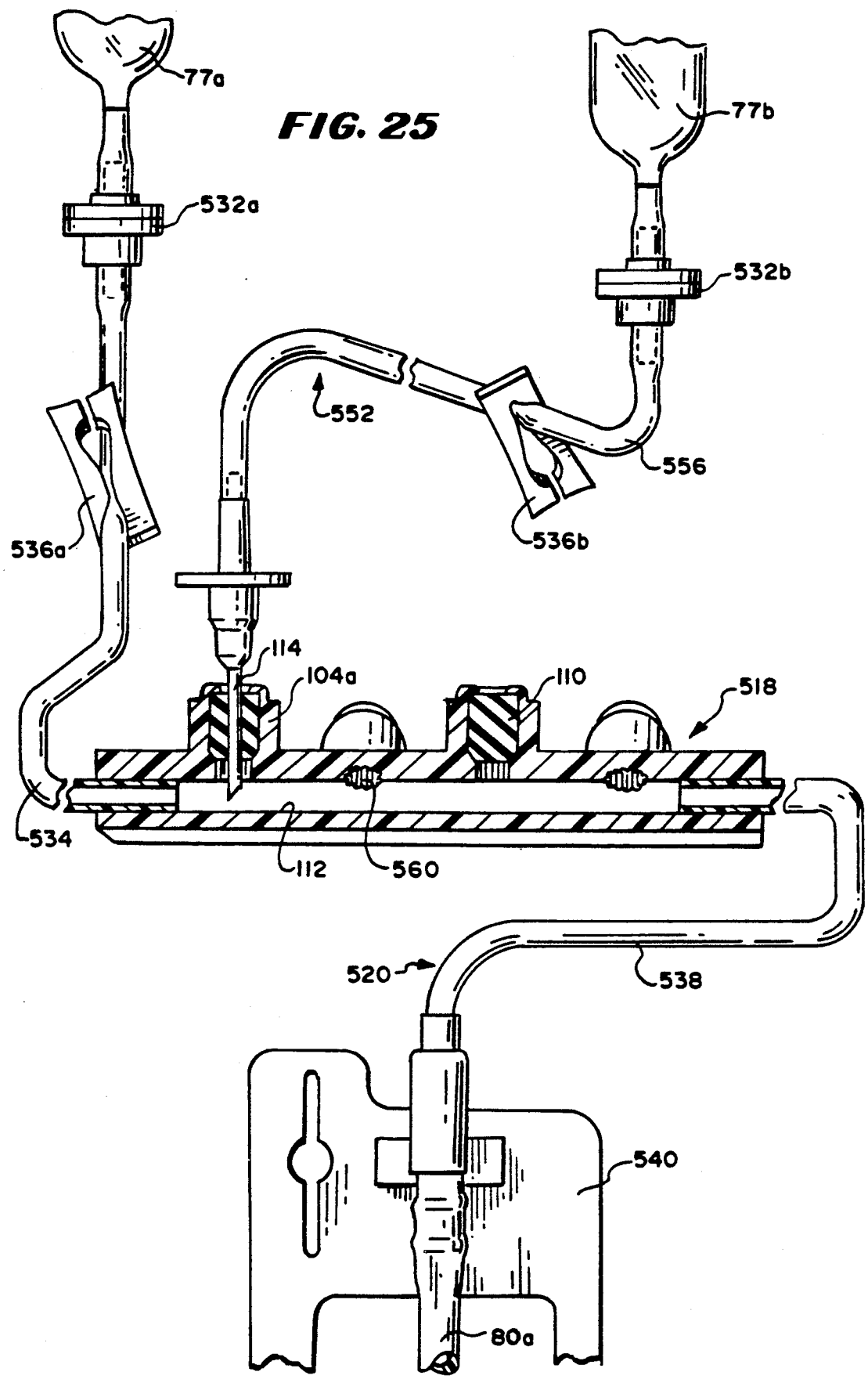

The tubing set 520 is best illustrated in FIG. 21. The tubing set 520 is connected to a container 56a with a spike connector 75a. The spike connector 75a is connected to the tubing segment 522 which in turn is connected to a drip chamber 77a. The drip chamber 77a is connected to a one-way valve 532a, to prevent any potential fluid backflow into the container 56a due to pressure differentials in the lines or tubing sets. The one-way valve 532a is connected to a tubing segment 534, which is connected to one end of the fluid junction member 518. The tubing segment 534 includes a tubing clamp 536a, which is utilized to allow priming of the tubing set 520.

The opposite end of the fluid junction member 518 is connected to a tubing segment 538, which is coupled to a pump bracket 540, which pump bracket 540 is mountable into the pump 84 or 86 and includes the pump tubing region 80a. The pump bracket 540 is coupled to a tubing segment 541, which is connected to a first reverse "Y" junction 542. It has been discovered that the reverse "Y" junction 542 traps less air and wastes less fluid than the conventional "Y" junction 90a or 90b, when air is removed from the junction 542 as required.

The "Y" junction 542 is connected to a tubing segment 543, which may include and end in a tubing connector 546 which accommodates a change in diameter of the tubing segment 543 and a next tubing segment 544. The tubing segments 543 or 544 preferably includes a roller type tubing clamp 548, which is utilized in manual operation to adjust the fluid flow rate. The tubing segment 544 is connected to a second conventional "Y" junction 90b. A short tubing segment 549 is couplable to a catheter, needle or other body entry device C and again can include a clamp 550.

The tubing set 520 including the fluid junction member 518 through the tubing segment 549 can be considered the primary tubing set. One or more secondary tubing sets 552 also can be coupled to one of a plurality of sealed input ports 104a. The tubing set 552 includes a spike 75b connecting the tubing set 552 to a fluid container 56b. The spike 75b is connected by a tubing segment 554 to a drip chamber 77b, a oneway valve 532b, a tubing segment 556 and to a cannula 114. The tubing segment 554 can include a clamp 536b.

The fluid junction members 516 and 518 each include a primary set connection and four input ports 104a, such that ten fluids can be administered to a patient sequentially, concurrently or intermittently as desired. The specific connections and details of the fluid junction member 518 are best illustrated referring to FIGS. 22-25.

The fluid junction member 518 includes an elongated housing 558 having a central passage or flow path 112 therein. Each of the ports 104 include a pierceable, resealable septum 110, which accepts the cannula 114 of the secondary sets 552. The ports 104a are alternately inclined to avoid interference with one another. The septums 110 are connected to grooved passageways 560, which grooves form capillaries to remove trapped air when the sets 520 are primed with fluid. The shape of the housing 558 is not critical, but preferably is formed with a minimum amount of material and with a minimal internal volume. The internal volume of the fluid junction member 518 can be on the order of 0.6 ml. The internal volume of the set 520, including the fluid junction member is 4.5 ml.

Figure 26:
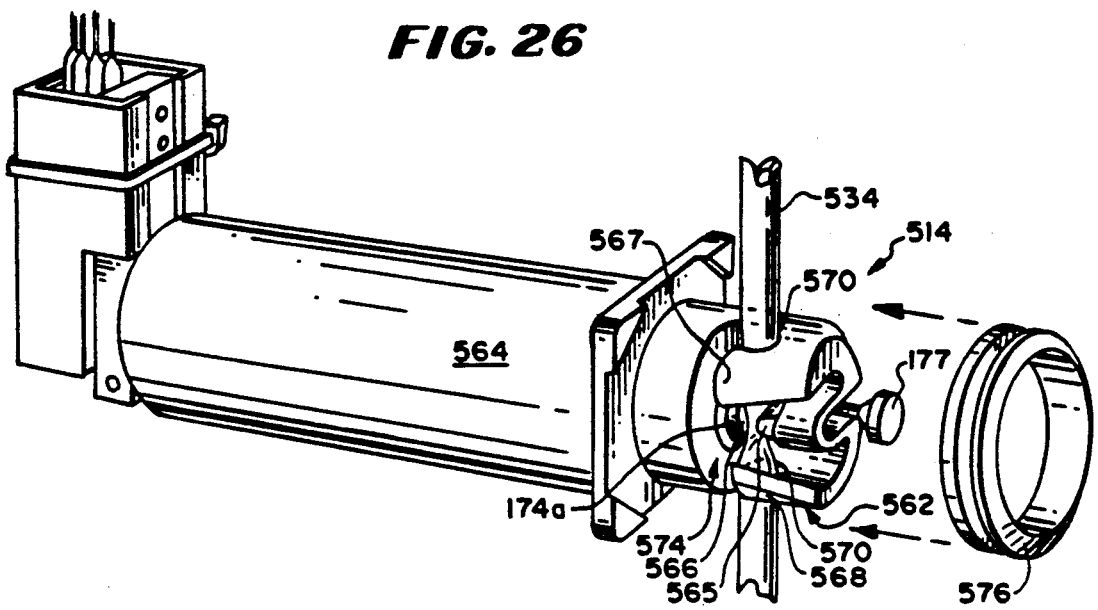
Figure 27:
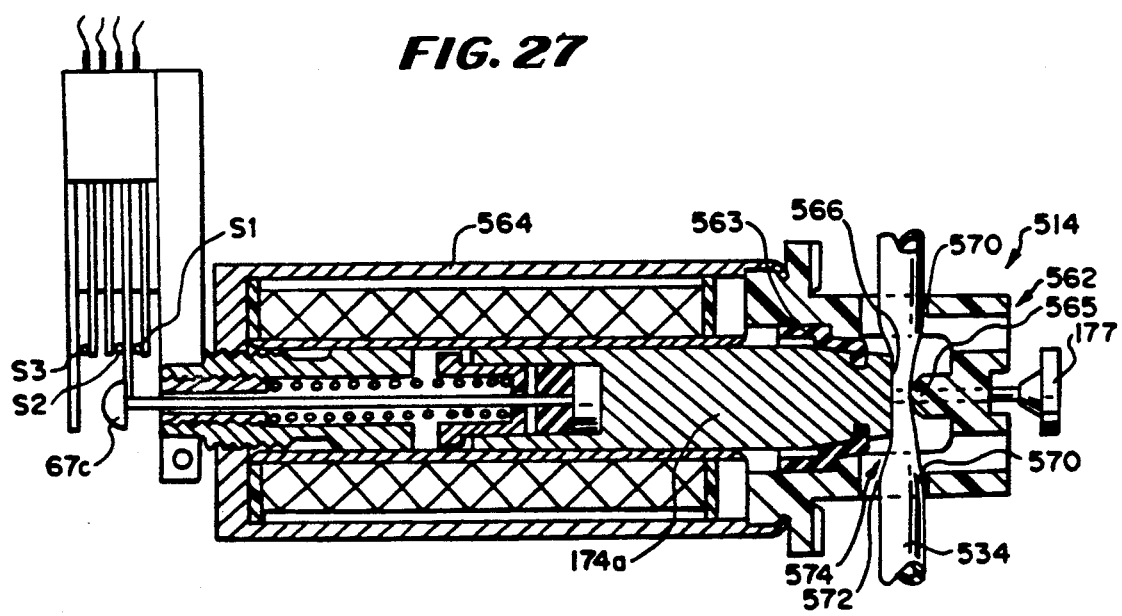

The occluders 514 are best illustrated in FIGS. 26 and 27. The occluders 514 are functionally equivalent to the occluders 64a, but include an improved tubing retaining structure or head 562. The head 562, preferably a one-piece, molded member, is sealingly mounted to a solenoid housing 564. As before, the occluder 514 includes a tubing clamping member 174a which biases the tubing segment 534 closed against an elongated transverse stop member 565 formed in the head 562. A round flat surface 566 forms an anvil for the stop member 565, allowing any orientation of the clamping member 174a. The axial and radial movement of the member 174a is provided for, while maintaining a fluid tight seal by an elastomeric seal 563, mounted between the head 562 and the member 174a. This is a distinct advantage over the prior clamping members, which generally include two opposing elongated surfaces (like the member 565), which could easily be misaligned and allow the tubing to slip out or only be partially clamped. When the occluder 514 is energized, the tubing clamping member 174a is retracted allowing fluid to flow or for the tubing segment 534 to be removed.

The head 562 includes a pair of arms 567 and 568, each of which include a recess 570, forming a passageway 572 for the tubing segment 534. The tubing segment 534 is loaded into the head 562 by actuating the occluder 514 or by manually depressing a knob 177, which is offset from the passageway 572 and bears against the tubing clamping member 174a. The tubing segment 534 is moved into or out of the passageway 572 through a slot 574. The offset passageway 572 prevents the tubing segment 534 from vibrating or otherwise inadvertently being dislodged from the operating position adjacent the tubing clamping member 174a. A sealing ring 576 is mounted over the head 562 to seal the occluder 514 from fluid leaking into the module 512.

As previously described, the clamping member 174a is connected to a position sensor 67c, which operates on a set of contacts S1, S2 and S3 to provide the system 500 with the actual location and operation of the clamping member 174a. S1 and S3 closed, with S2 open indicates the member 174a is closed against the member 565 with no tubing clamped therebetween. S3 closed and S1 and S2 open indicates the member 174a is closed with tubing clamped therebetween. The fully open and fluid flow position has S1 and S3 open and S2 closed. S2 and S3 closed with S1 open indicates that the occluder 514 is inoperative.

The system 500 thus can schedule quantities of as small as one-eighth ml of fluid to arrive at a patient through one of two lines from up to ten different drugs through the two fluid junction members 516 and 518. The fluids can be delivered sequentially or concurrently, mixed or segmented as desired. The system 500 manages the fluids in the tubing set 520 to ensure that the proper sequence and flow of fluids reaches the patient at the appropriate time by accounting for all fluid in the tubing set 520. Further, the system 500 utilizes very small tubing to minimize the fluid volume in the tubing set 520 and to deliver the fluids and hence the drugs to the patient in the minimal time period.

The system 500 is autoprimed by preproportioning the fluid in the tubing set 520 so that the proper rate and ratio of fluids is delivered to the patient upon initiation of the system 500. Further, the small line or tubing set 520 size, preferably utilizes a volume of only 4.5 to 9 ml of fluid to minimize waste and flow time. The tubing can be on the order of 0.040 to 100 inches in internal diameter. The fluid junction members 516 and 518 have a minimal sized inner flow passage 112, again to minimize the volume of fluid in the tubing set 520.

By accounting for the fluid in the tubing set 520, the system 500 provides advantages over even single fluid delivery systems which do not account for the volume of the tubing set or the different fluids/drugs in the tubing set. The system 500 provides the proper flow and fluids at the patient, rather than at the fluid container or at the pump, which, as stated above, can be a large difference in flow rates.

The sizes and internal volume of the prior art system were selected to provide a specific example, as discussed with respect to FIGS. 1A and 1B. In general, the prior systems do not take into account the fluid volumes and mixtures in the tubing system and do not specify any particular sizes. By preconfiguring the fluid mixture in advance, knowing the flow rates and the volume of the fluid set 520, the system 500 ensures the proper mixture and flow rate at the patient delivery site C.

The system 500 includes as a part of the control system 142, diagnostic software which is utilized prior to every startup of the system 500 to test all the hardware components and operation software to ensure that the system 500 is fully operable.

Many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A multi-fluid delivery system for delivering one or a plurality of fluids, said system comprising:
    a mobile base having a standard mounted thereon;
    said standard having mounted thereon, fluid container mounting means, drip detection means, an array of occluder means, a fluid junction having a plurality of input ports and one output port and at least one pumping means;

a primary tubing set comprising a plurality of tubing segments;

at least one fluid container mounted on said fluid container mounting means, said fluid container coupled to one of said fluid junction input ports by said primary tubing set;

said primary tubing set including a drip chamber coupled to said drip detection means and coupled to said fluid junction by a primary tubing set segment coupled through one of said occluder means;

said fluid junction formed as a rigid body including an elongated housing having an internal fluid flow passageway therein opening at both ends defining input and output ports, at least one reusable port communicating with said passageway adapted to have a cannula of a secondary tubing segment of a secondary fluid container and tubing set coupled thereto, said at least one reusable port including septum means and including a plurality of grooves about the inner periphery, of the passageway therein adjacent said septum means to assist in removing air from said fluid junction, and means for mounting said housing to said standard;

said fluid junction coupled through said pumping means to a patient delivery means by a tubing segment connected to said fluid junction output port.

2. The system as defined in claim 1 including a secondary fluid container mounted on said fluid container mounting means, said secondary fluid container coupled to said fluid junction by a secondary tubing set and each said tubing set including a drip chamber coupled to said drip detection means and coupled to said fluid junction by a tubing segment coupled through one of said occluder means.

3. The system as defined in claim 2 wherein a first one of said tubing sets is a primary tubing set connected to a fixed input port of said fluid junction and said secondary second tubing set is coupled to said fluid junction through a cannula inserted through a reusable port in said fluid junction.

4. The system as defined in claim 1 wherein said fluid junction output port tubing segment is mounted through a cassette, which cassette is configured to be mounted in said pumping means.

5. The system as defined in claim 1 wherein said occluder means include a tubing segment retaining head, said head including an offset passageway to prevent inadvertent loss of said tubing set.

6. The system as defined in claim 5 wherein said head further includes an elongated transverse stop member on one side of said passageway and said occluder means include clamping member means operable against said elongated transverse stop member, said clamping member means including a round flat anvil surface adapted to bear against said tubing segment in said passageway.

7. The system as defined in claim 1 wherein said fluid junction includes a mounting flange and said array of occluder means includes a bracket mounted to said standard with said mounting flange mountable therein.

8. The system as defined in claim 1 wherein said drip detection means are mounted in a fixed position on said standard.

9. The system as defined in claim 1 further including control means operable to perform diagnostic testing of the operation of the system prior to actual system operation.

10. The system as defined in claim 1 further including means for accounting for the volume and type of fluid in said tubing set.

11. The system as defined in claim 1 further including control means including means for entering fluid delivery data to said control means and means for monitoring the system operation.

12. The system as defined in claim 11 further including means for printing the system operation data including the current status of the system operation, said printing means including buffer means for storing the system operation data updated by said control means.

13. The system as defined in claim 12 wherein said primary tubing set has a fixed volume between said fluid junction and said patient connecting means and including said fluid junction.

14. The system as defined in claim 12 wherein said printing means include means for printing out said system operation data automatically upon occurrence of a malfunction of the system operation.

15. The system as defined in claim 11 wherein said tubing set includes a primary tubing set including a spike for connecting said primary tubing set to said fluid container, said spike coupled to said drip chamber, a first flexible tubing segment coupling said drip chamber to said fluid junction, said fluid junction including at least one resealable input port and at least one output port, a second flexible tubing segment having a pumping region therein coupled to said pumping means and coupling to said fluid junction output port and coupled to at least a first Y-type connector and a third flexible tubing segment adapted to coupled said Y-type connector to patient connecting means.

16. The system as defined in claim 15 including a fourth flexible tubing segment coupling said spike to said drip chamber, a one-way valve coupled between said drip chamber and said fluid junction, said second tubing segment pumping region mounted in a pump bracket, an inverse Y-type connector coupled to said second flexible tubing segment and a fifth flexible tubing segment coupled to aid first Y-type connector.

17. The system as defined in claim 16 further including a secondary tubing set including a spike for connecting said secondary tubing set to a secondary fluid container, said spike coupled to secondary drip chamber, a first secondary flexible tubing segment including a cannula coupling said second drip chamber to said resealable input port of said fluid junction, a second secondary flexible tubing segment coupling said spike to said second drip chamber and a one-way valve coupled between said second drip chamber and said fluid junction.

18. The system as defined in claim 1 wherein said fluid junction includes a plurality of sealable fluid input ports offset to one another along one side of said housing and adapted to be coupled to a cannula of a tubing segment of a secondary tubing set.

19. The system as defined in claim 1 wherein said mounting means include a mounting flange formed on another side of said housing adapted to be mounted to a fixed mounting slot on said standard.

20. A multi-fluid delivery system for delivering one or a plurality of fluids, said system comprising:

a mobile base having a standard mounted thereon;

said standard having mounted thereon, fluid container mounting means, drop detection means, array of occluder means, a pair of fluid junctions, each junction having a plurality of input ports and one output port and at least two pumping means;

each said fluid junction formed as a rigid body including an elongated housing having an internal fluid flow passage therein opening at both ends of said housing defining input and output ports, at least one reusable port adapted to have a cannula of a second tubing segment of a secondary fluid container and secondary tubing set coupled thereto, said at least one reusable port including a septum means and including a plurality of grooves about the inner periphery of the passageway therein adjacent to said septum means to assist in removing air from said fluid junction, and means for mounting said housing to said standard;

at least two fluid containers mounted on said fluid container mounting means, each said fluid container coupled to a respective one of said fluid junctions by a tubing set;

each said tubing set including a drip chamber coupled to said drip detection means and coupled to said respective fluid junction input port by a tubing segment coupled through one of said occluder means; and each one of said fluid junctions coupled through one of said pumping means to a patient delivery means by a respective tubing segment connected to a respective fluid junction output port.

21. The system as defined in claim 20 including a second fluid container mounted on said fluid container mounting means coupled to a first one of said fluid junctions by a secondary tubing set and each said secondary tubing set including a drip chamber coupled to said drip detection means and coupled to said first fluid junction by a secondary tubing segment coupled through one of said occular means.

22. The system as defined in claim 21 wherein a first one of said tubing sets is a primary tubing set connected to a fixed input port of said first fluid junction and said second tubing set is coupled to said first fluid junction through a cannula inserted through a reusable port in said first fluid junction.

* * * * *